US010077474B2

(12) United States Patent
Huang et al.

(10) Patent No.: US 10,077,474 B2
(45) Date of Patent: Sep. 18, 2018

(54) METHOD OF DESIGNING PRIMERS, METHOD OF DETECTING SINGLE NUCLEOTIDE POLYMORPHISMS (SNPS), METHOD OF DISTINGUISHING SNPS, AND RELATED PRIMERS, DETECTABLE OLIGONUCLEOTIDES, AND KITS

(71) Applicant: Abbott Molecular Inc., Des Plaines, IL (US)

(72) Inventors: Shihai X. Huang, Lincolnshire, IL (US); Hong X. Su, Evanston, IL (US); Brian J. Erickson, Kenosha, WI (US)

(73) Assignee: Abbott Molecular, Inc., Des Plaines, IL (US)

( * ) Notice: Subject to any disclaimer, the term of this patent is extended or adjusted under 35 U.S.C. 154(b) by 595 days.

(21) Appl. No.: 13/840,142

(22) Filed: Mar. 15, 2013

(65) Prior Publication Data

US 2013/0323727 A1 Dec. 5, 2013

Related U.S. Application Data

(60) Provisional application No. 61/652,827, filed on May 29, 2012.

(51) Int. Cl.
| | | |
|---|---|---|
| *C12Q 1/68* | (2018.01) | |
| *C12Q 1/6876* | (2018.01) | |
| *C12Q 1/6886* | (2018.01) | |
| *C12Q 1/6858* | (2018.01) | |

(52) U.S. Cl.
CPC ......... *C12Q 1/6876* (2013.01); *C12Q 1/6858* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS

| 7,250,289 B2* | 7/2007 | Zhou | C12Q 1/6837 |
| | | | 435/287.2 |
| 7,378,232 B2 | 5/2008 | Orlow et al. | |
| 7,442,507 B2 | 10/2008 | Polsky et al. | |
| 2004/0121374 A1 | 6/2004 | Iwaki et al. | |
| 2005/0026164 A1 | 2/2005 | Zhou | |
| 2005/0214753 A1 | 9/2005 | Shultz et al. | |
| 2006/0252041 A1 | 11/2006 | Batt | |
| 2007/0020657 A1 | 1/2007 | Grebe et al. | |
| 2007/0087350 A1 | 4/2007 | Kappel | |
| 2008/0176226 A1* | 7/2008 | Chiou | C12Q 1/6827 |
| | | | 435/6.14 |
| 2009/0181371 A1 | 7/2009 | Samowitz et al. | |
| 2010/0009355 A1 | 1/2010 | Kolodney | |
| 2010/0173294 A1 | 7/2010 | Langland et al. | |
| 2011/0158944 A1 | 6/2011 | Hosted et al. | |
| 2011/0212991 A1 | 9/2011 | Langland et al. | |
| 2011/0230360 A1 | 9/2011 | Stephan et al. | |
| 2011/0236916 A1 | 9/2011 | Zou et al. | |
| 2011/0269124 A1* | 11/2011 | Stephens | C12Q 1/6886 |
| | | | 435/6.11 |

FOREIGN PATENT DOCUMENTS

| JP | 2004121087 A | 4/2004 | |
| JP | 2010528585 A | 8/2010 | |
| WO | 2005027710 A2 | 3/2005 | |
| WO | 2005059171 A1 | 6/2005 | |
| WO | 2005066346 A1 | 7/2005 | |
| WO | 2005071109 A1 | 8/2005 | |
| WO | 2007009013 A2 | 1/2007 | |
| WO | WO 2007002325 A1 * | 1/2007 | ............ C07C 37/62 |
| WO | 2008106453 A2 | 9/2008 | |
| WO | 2009073513 A1 | 6/2009 | |
| WO | 2010011884 A2 | 1/2010 | |
| WO | 2010097020 A1 | 9/2010 | |
| WO | 2011019704 A2 | 2/2011 | |
| WO | 2011103770 A1 | 9/2011 | |
| WO | 2011106298 A1 | 9/2011 | |
| WO | WO 2011103770 A1 * | 9/2011 | .......... C12Q 1/6886 |
| WO | 2011131146 A1 | 10/2011 | |
| WO | 2012028746 A1 | 3/2012 | |

OTHER PUBLICATIONS

Stratagene Catalog. gene characterization kits. Stratagene Catalog, p. 39, 1988.*
Lowe et al., A computer program for selection of oligonucleotide primers for polymerase chain reactions. Nucleic Acids Research, vol. 18, No. 7, pp. 1757-1761, 1990.*
Hoorfar et al. (2004) doi: 10.1128/JCM.42.5.1863-1868.2004 J. Clin. Microbiol. May 2004 vol. 42 No. 5 1863-1868.*
Kebebew, et al. "The Prevalence and Prognostic Value of BRAF Mutation in Thyroid Cancer", Annals of Surgery, vol. 246, No. 3, Sep. 2007, pp. 466-471.
International Search Report with Written Opinion dated Nov. 12, 2013 in corresponding International Patent Application No. PCT/US13/42817 (15 pages).
Davies, et al. "Mutations of the BRAF gene in human cancer", Nature, Jun. 27, 2002, vol. 417, pp. 949-954 (6 pages).
Kimura, et al. "High Prevalence of BRAF Mutations in Thyroid Cancer", Cancer Res, Apr. 1, 2003, vol. 63, pp. 1454-1457 (11 pages).
Shinozaki, et al. "Utility of Circulating B-RAF DNA Mutation in Serum for Monitoring Melanoma Patients Receiving Biochemotherapy" Clin. Cancer Res., Apr. 1, 2007, vol. 13, No. 7, pp. 2068-2074 (15 pages).
Benlloch, et al. "Detection of BRAF V600E Mutation in Colorectal Cancer", Journal of Molecular Diagnostics, Nov. 5, 2006, vol. 8, No. 5, pp. 540-543 (4 pages).
Hay, et al. "BRAF Mutations in Melanocytic Lesions and Papillary Thyroid Carcinoma Samples Identified Using Melting Curve Analysis of Polymerase Chain Reaction Products" Arch. Pathol. Lab. Med., Sep. 2007, vol. 131, pp. 1361-1367 (7 pages).

(Continued)

*Primary Examiner* — Suchira Pande
(74) *Attorney, Agent, or Firm* — Pierce Atwood LLP; Kevin M. Farrell; David J. Wilson

(57) ABSTRACT

A method of designing a primer for detecting a single nucleotide polymorphism (SNP), a method of detecting an SNP, a method of distinguishing SNPs, primers, detectable oligonucleotides, and kits.

10 Claims, 7 Drawing Sheets

Specification includes a Sequence Listing.

(56) References Cited

OTHER PUBLICATIONS

Sapio, et al. "Detection of BRAF mutation in thyroid papillary carcinomas by mutant allele-specific PCR amplification (MASA)", European Journal of Endocrinology, Feb. 1, 2006, vol. 154, pp. 341-348 (8 pages).

Jarry, et al. "Real-time allele-specific amplification for sensitive detection of the BRAF mutation V600E" Molecular and Cellular Probes, May 18, 2004, vol. 18, pp. 349-352 (4 pages).

Turner, et al. "Detection of the BRAF V600E mutation in melanocytic lesions using the ligase detection reaction" Journal of Cutaneous Pathology, 2005, vol. 32, pp. 334-339 (6 pages).

Kirby, et al. "Allele-Specific PCR Analysis of p53 Codon 249 AGT Transversion in Liver Tissue from Patients with Viral Hepatitis" Int. Journal Cancer; 1996; vol. 68; pp. 21-25.

Hamfjord, et al. "Wobble-enhanced ARMS method for detection of KRAS and BRAF mutations" Diagnostic Molecular Pathology; Sep. 2011; vol. 20; No. 3; pp. 158-165.

Ellison, et al. "A comparison of ARMS and DNA sequencing for mutation analysis in clinical biopsy samples" Journal of Experimental & Clinical Cancer Research; 2010; vol. 29; No. 132; pp. 1-8.

Clinical DNA diagnostic method, 1st edition, published by Kanehara & Co., Ltd. on Jul. 1, 1995, pp. 175-177.

\* cited by examiner

Wild-type Target -----AAATAGGTGATTTTGGTCTAGCTACA<u>GTG</u>AAATCTCGATGG----- [SEQ ID NO: 1]

Detection of V600E:

V600E Target:       -----AAATAGGTGATTTTGGTCTAGCTACA<u>GAG</u>AAATCTCGATGG----- [SEQ ID NO: 2]
                                       OR
                    -----AAATAGGTGATTTTGGTCTAGCTACA<u>GAA</u>AAATCTCGATGG----- [SEQ ID NO: 3]

Forward Primer 1    5' AATAGGTGATTTTGGTCTAGCTACC<u>GAG</u> 3' [SEQ ID NO: 8]
Forward Primer 2    3' AATAGGTGATTTTGGTCTAGCTACC<u>GAA</u> 3' [SEQ ID NO: 9]

Wild-type PNA                           N- GCTACA<u>GTG</u>AAATCTCG -C [SEQ ID NO: 12]
V600K PNA                               N- GCTACA<u>AAG</u>AAATCTCG -C [SEQ ID NO: 13]

Detection of V600K:

V600K Target:       -----AAATAGGTGATTTTGGTCTAGCTACA<u>AAG</u>AAATCTCGATGG----- [SEQ ID NO: 4]
                                       OR
                    -----AAATAGGTGATTTTGGTCTAGCTACA<u>AAA</u>AAATCTCGATGG----- [SEQ ID NO: 5]

Forward Primer 1    5' AATAGGTGATTTTGGTCTAGCTACT<u>AAG</u> 3' [SEQ ID NO: 17]
Forward Primer 2    3' AATAGGTGATTTTGGTCTAGCTACT<u>AAA</u> 3' [SEQ ID NO: 18]

Wild-type PNA                           N- GCTACA<u>GTG</u>AAATCTCG -C [SEQ ID NO: 12]
V600E PNA                               N- GCTACA<u>GAG</u>AAATCTCG -C [SEQ ID NO: 19]

Detection of V600D:

V600D Target:       -----AAATAGGTGATTTTGGTCTAGCTACA<u>GAT</u>AAATCTCGATGG----- [SEQ ID NO: 6]
                                       OR
                    -----AAATAGGTGATTTTGGTCTAGCTACA<u>GAC</u>AAATCTCGATGG----- [SEQ ID NO: 7]

Forward Primer 1    5' AATAGGTGATTTTGGTCTAGCTACT<u>GAT</u> 3' [SEQ ID NO: 20]
Forward Primer 2    3' AATAGGTGATTTTGGTCTAGCTACT<u>GAC</u> 3' [SEQ ID NO: 21]

Wild-type PNA                           N- GCTACA<u>GTG</u>AAATCTCG -C [SEQ ID NO: 12]

Allele specific primer design strategies

| Example | Forward or Reverse Primer Design (as shown by the 5'→3' oligonucleotide) | Keys to Primer Design Graph |
|---|---|---|
| 1. There is one SNP of interest. There are no other mutations (somatic or allelic) adjacent to the SNP of interest. | 3'-X-X-X-X-X-X-X-X-X-X-X-X-X-X 5'<br>5'-X-X-X-X-X-X-X-X-X-X-X-X-X 3'<br><br>3'-X-X-X-X-X-X-X-X-X-X-X-X-X-X 5'<br>5'-X-X-X-X-X-X-X-X-X-X-X-X-X 3' | Template sequences are shown from 3'→5'. Primer sequences are shown from 5'→3'.<br><br>"X" designates nominal bases on either strand. Nominal base is defined as the natural occurring bases with no or insignificant occurrences of allele variations or mutations.<br><br>Red letter indicates bases that are different from the nominal template. The actual base type and position may vary.<br><br>Blue shaded base indicates the intentional mismatch as part of primer design. The actual position relative to 3' end may vary between 2 and 6. |
| 2. There is one SNP of interest. There are other mutations adjacent to the SNP of interest. These adjacent mutations should not affect the result of the SNP of interest. | Design of multiple primers is needed.<br><br>3'-X-X-X-X-X-X-X-X-X-X-X-X-X-X 5'<br>3'-X-X-X-X-X-X-X-X-X-X-X-X-X-X 5'<br>3'-X-X-X-X-X-X-X-X-X-X-X-X-X-X 5'<br>3'-X-X-X-X-X-X-X-X-X-X-X-X-X-X 5'<br>5'-X-X-X-X-X-X-A-X-X-X-X 3'<br>5'-X-X-X-X-X-X-C-X-X-X-X 3'<br>5'-X-X-X-X-X-X-G-X-X-X-X 3'<br>5'-X-X-X-X-X-X-T-X-X-X-X 3'<br><br>3'-X-X-X-X-X-X-X-X-X-X-X-X-X-X 5'<br>3'-X-X-X-X-X-X-X-X-X-X-X-X-X-X 5'<br>3'-X-X-X-X-X-X-X-X-X-X-X-X-X-X 5'<br>3'-X-X-X-X-X-X-X-X-X-X-X-X-X-X 5'<br>5'-X-X-X-X-T-X-A-X-X-X-X 3'<br>5'-X-X-X-X-T-X-C-X-X-X-X 3'<br>5'-X-X-X-X-T-X-G-X-X-X-X 3'<br>5'-X-X-X-X-T-X-T-X-X-X-X 3' | "MM" indicates mismatches between a primer and a template. Template sequences are shown from 3'→5'. Primer sequences are shown from 5'→3'.<br><br>"X" designates nominal bases on either strand. Nominal base is defined as the natural occurring bases with no or insignificant occurrences of allele variations or mutations.<br><br>Red letter indicates bases that are different from the nominal template. The actual base type and position may vary.<br><br>Blue shaded base indicates the intentional mismatch as part of primer design. The actual position relative to 3' end may vary between 2 and 6.<br><br>"MM" indicates mismatches between a primer and a template.<br><br>NOTE: There can be a scenario where there are "neutral" SNPs adjacent to the SNPs of interest. These "neutral" SNPs can have 4 possible alleles, A, C, T, G and should have no impact on the assay result. This example has the neutral SNP at the 2nd base 5' to the SNP of interest.<br><br>NOTE: The position of "neutral" SNPs adjacent to SNP of interest do not necessary cover all 4 possible bases. The position as shown only represents one possible position.<br><br>NOTE: The possible "neutral" SNPs can be any position adjacent to the SNP of interest either 5' or 3' to the SNP of interest. The number and sequences of designed primers should correspond to the number and identities of the mutations. |

Figure 2 Cont.

Allele specific primer design strategies (continued)

| Scenario | Forward or Reverse Primer Design (as shown by the 5'→3' oligonucleotide) | Keys to Primer Design Graph |
|---|---|---|
| 3. There are multiple SNP of interest in the same position. All possible SNPs should be detected. | Design of multiple primers is needed. | Template sequence is shown from 3'→5'. Primer sequences are shown from 5'→3'.<br><br>"X" designates nominal bases on either strand. Nominal base is defined as the natural occurring bases with no or insignificant occurrences of allele variations or mutations.<br><br>Red letter indicates bases that are different from the nominal template. The actual base type and position may vary.<br><br>Blue shaded base indicates the intentional mismatch as part of primer design. The actual position relative to 3' end may vary between 2 and 6.<br><br>"M" indicates mismatches between primer and template.<br><br>NOTE: Two SNP possibilities are shown in the position of interest as an example. The actual situations may have 4 SNP possibilities.<br>NOTE: There can be a scenario where there are "neutral" SNPs adjacent to the SNPs of interest. These "neutral" SNPs should have no impact on the assay result. A possible solution would be the design concept in scenario 2. |
| 4. There are multiple SNPs of interest in multiple positions, with one SNP per position. Simultaneous presence of multiple SNPs in a given sample should be detected. The single SNP should not be detected. | | Template sequence is shown from 3'→5'. Primer sequences are shown from 5'→3'.<br><br>"X" designates nominal bases on either strand. Nominal base is defined as the natural occurring bases with no or insignificant occurrences of allele variations or mutations.<br><br>Red letter indicates bases that are different from the nominal template. The actual base type and position may vary.<br><br>Blue shaded base indicates the intentional mismatch as part of primer design. The actual position relative to 3' end may vary between 2 and 6.<br><br>"M" indicates mismatches between primer and template.<br><br>NOTE: The number of SNPs of interest is two in this example. The actual number of SNPs may vary.<br>NOTE: The SNPs are shown in the position of interest as an example. The actual positions may vary. |

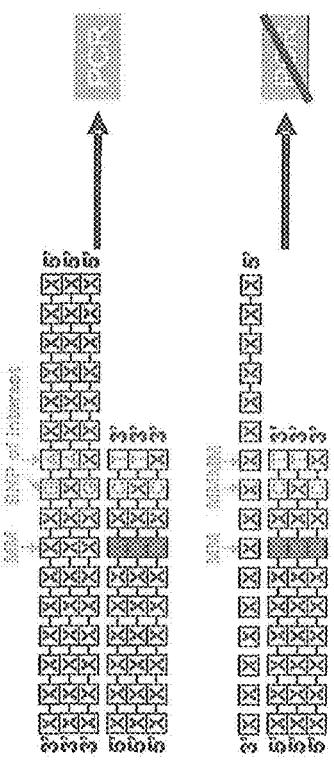
Figure 2 Cont.
Figure 3 Schematic illustration of amino acid specific design principle using BRAF V600E as a model target
Note: n may be any base other than the one in the targeted region

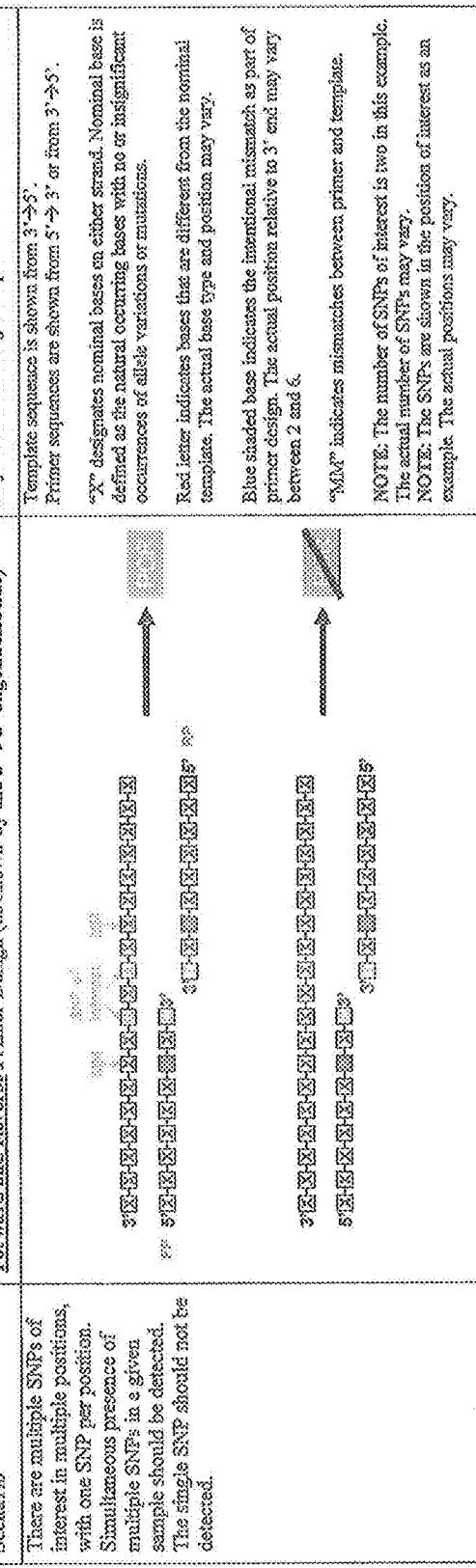

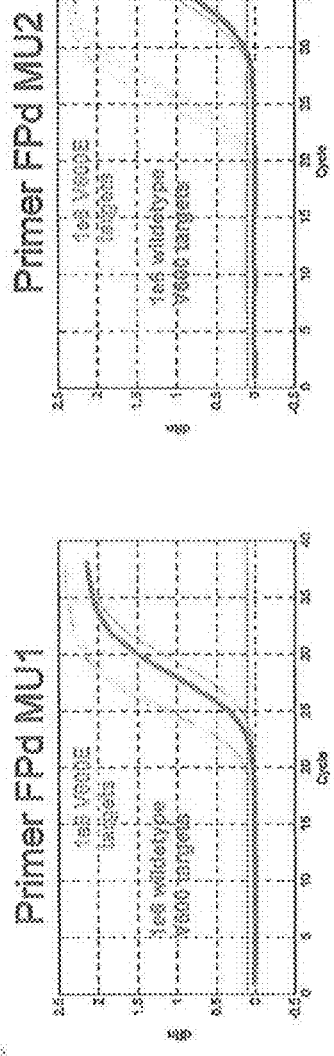

| ACT 600c | WT1799a | T1799Aa | V600Ea | V600Ea1 | V600Ea2 | V600Ra | 599 115 | V600Na |
|---|---|---|---|---|---|---|---|---|
| | GTG Val(V) | GAG Glu(E) | GAA Glu(E) | A/G Lys(K) | AAA Lys(K) | A/G Arg(R) | GAT Asp(D) | AAC/T Asn(N) |
| MUT1b...ACC GAG | | | | | | | | |
| # of mismatches | 2 | 1 | 2 | 2 | 3 | 3 | 2 | 3 |
| Position (from 3') | 4,2 | 2 | 4,1 | 4,3 | 4,3,1 | 4,3,2 | 4,1 | 4,3,1 |
| dCt | 9.38 | 0 | 9.28 | 7.87 | 13.98 | 8.92 | 11.33 | 17.98 |
| MUT2b...ACC GAA | | | | | | | | |
| # of mismatches | 3 | 2 | 1 | 3 | 2 | 4 | 2 | 3 |
| Position (from 3') | 4,2,1 | 4,1 | 2 | 4,3,1 | 4,3 | 4,3,2,1 | 4,1 | 4,3,1 |
| dCt | 11.78 | 7.81 | 0 | 7.38 | 6.9 | 19.3 | 18.73 | 7.82 |
| MUT3c...ACG AAG | | | | | | | | |
| # of mismatches | 3 | 2 | 3 | 1 | 2 | 2 | 3 | 2 |
| Position (from 3') | 4,3,2 | 4,3 | 4,3,1 | 2 | 4,1 | 4,3 | 4,3,1 | 4,1 |
| dCt | 13.87 | 3.68 | 8.74 | 0 | 8.18 | 1.3 | 17.88 | 10.38 |
| MUT4a...ACT AAA | 4 | 3 | 2 | 2 | 1 | 3 | 3 | 2 |
| | 4,3,2,1 | 4,3,1 | 4,3 | 4,1 | 2 | 4,3,1 | 4,3,1 | 4,1 |
| dCt | 13.13 | 13.38 | 6.89 | 4.7 | 0 | 9.47 | 15.88 | 7.88 |

Figure 8

METHOD OF DESIGNING PRIMERS, METHOD OF DETECTING SINGLE NUCLEOTIDE POLYMORPHISMS (SNPS), METHOD OF DISTINGUISHING SNPS, AND RELATED PRIMERS, DETECTABLE OLIGONUCLEOTIDES, AND KITS

SEQUENCE LISTING

The instant application contains a Sequence Listing which has been submitted in ASCII format via EFS-Web and is hereby incorporated by reference in its entirety. Said ASCII copy, created on Jun. 26, 2013, is named 01886-2005US02_SL.txt and is 17,592 bytes in size.

TECHNICAL FIELD

The present disclosure relates to a method of designing primers, methods of detecting/distinguishing single nucleotide polymorphisms (SNPs), primer extension (e.g., polymerase chain reaction (PCR) and isothermal extension), peptide nucleic acids (PNAs), use of PNAs as PCR clamps, primers, detectable oligonucleotides, and kits.

BACKGROUND

Many genetic variations (including germ-line and somatic mutations) are important markers for hereditary abnormality, disease progression and therapeutic efficacy. Molecular diagnostic assays based on various technologies have been or are being developed to detect single nucleotide polymorphisms (SNPs). One of the widely adopted methods is allele specific polymerase chain reaction (AS-PCR) in which allele specific primers are designed to amplify variant specific targets based on the selective extension by polymerase according to the 3' matching between the primer and its template. Specifically, PCR amplification is only sufficiently effective where there are no or very few mismatches between the primer and its template at or near the 3' end of the primer, whereas PCR amplification is not detectable when the number of mismatches at or near the 3' end of the primer is sufficient to disrupt effective binding of the primer to the template.

The sensitivity and specificity of such methods significantly depend on the differential PCR efficiencies between the templates containing the SNPs of interest and non-targeted templates containing other sequences, including other alleles in the case of germ-line mutations and wild-type (or other mutations) in the case of somatic mutations. When the difference in PCR efficiency between the targeted and non-targeted templates is insufficient, there may be detectable amplification on the non-targeted template (non-specific signals), and the non-specific amplification signals (e.g., Ct or signal strength), albeit less efficient, can be too close to the specific signals (e.g., Ct or signal strength) to fully separate low level of specific targets from the non-specific targets. In such cases, it is difficult to establish assay cut-off to achieve both high level sensitivity and specificity. The technical requirement of fully differentiated PCR efficiencies is particularly critical in areas where very low mutant contents need to be detected from the samples, such as many onocology-associated somatic mutations.

The BRAF gene, an example of a gene having an oncology-associated somatic mutation, encodes a protein belonging to the raf/mil family of serine/threonine protein kinases (namely, serine/threonine-protein kinase B-raf). B-raf plays a role in regulating the MAPK (mitogen-activated protein kinase) signaling pathway, which affects cell division, cell differentiation, and secretion. Germ-line mutations in the BRAF gene are associated with cardiofaciocutaneous syndrome, which is characterized by heart defects, a distinctive facial appearance, and mental retardation. Mutations in the BRAF gene are also associated with various types of cancers, including adenocarcinoma of the lung, colorectal cancer, malignant melanoma, non-Hodgkin's lymphoma, non-small cell lung carcinoma, and thyroid carcinoma.

Mutation of thymine at nucleotide position 1796 to adenine has been detected in lung cancers and head and neck cancers (U.S. Pat. No. 7,378,233; see U.S. Pat. No. 7,442,507 for T1799A). Detection of T1796A in exon 15 of the BRAF gene reportedly enables a malignant papillary thyroid neoplasm to be distinguished from a benign thyroid sample (U.S. Pat. No. 7,378,233) and also enables distinction of HNPCC tumors from sporadic colorectal tumors (Int'l Pat. App. Pub. No. WO 2005/071109). Detection of T1799A reportedly indicates the presence of metastatic melanoma (U.S. Pat. App. No. 2006/0246476, now U.S. Pat. No. 7,442,507).

Most mutations in the BRAF gene associated with cancers occur at amino acid position 600, which is located in the activation domain. Amino acid position 600 also has been referred to as amino acid position 599 in the literature. Mutation of valine (V) at amino acid position 600 to glutamic acid (E) (see, e.g., U.S. Pat. App. Pub. No. 2007/0020657, Davies, et al., Nature 417: 949-954 (2002), in which it is designated V599E, and Kimura, et al., Cancer Res. 63: 1454-1457 (2003)), lysine (K), or aspartic acid (D) accounts for more than 90% of all mutations in the BRAF gene. The presence of a colorectal neoplasm reportedly can be determined by detecting a point mutation in an exfoliated epithelial marker, such as BRAF, along with one or more fecal occult blood markers (see U.S. Pat. App. Pub. No. 2011/0236916). Analysis of BRAF mutations, along with microsatellite stability, reportedly enables prognosis of survival rates in patients with cancer as well as classification of severity of cancer in patients (see Int'l Pat. App. Pub. No. WO 2007/009013 and U.S. Pat. App. Pub. No. 2009/0181371). See, e.g., U.S. Pat. App. Pub. No. 2011/0269124 and Int'l Pat. App. Pub. No. WO 2011/019704 for detection of BRAF mutations generally. Mutation in codon 599 of exon 15 of BRAF reportedly enables the detection of malignant melanoma (see U.S. Pat. App. Pub. No. 2007/0087350; see, also, Int'l Pat. App. Pub. Nos. WO 2010/097020, WO 2005/027710, WO 2005/059171, and WO 2005/066346). The use of real-time polymerase chain reaction (PCR) clamping based on peptide nucleic acid (PNA) to detect mutations in codon 600 in BRAF is described in Int'l Pat. App. Pub. No. WO 2011/093606, whereas the use of allele-specific real-time quantitative PCR (AS-QPCR) using locked nucleic acid primers and beacon detectable oligonucleotides to detect V600E mutations in BRAF is described in Int'l Pat. App. Pub. No. WO 2011/104694 and the use of fluorescent quantitative PCR to detect mutations in the BRAF gene is described in Int'l Pat. App. Pub. No. WO 2011/103770. Liquid chips for detecting a V600E mutation in the BRAF gene are described in Int'l Pat. App. Pub. No. WO 2011/131146. Therefore, the ability to detect single nucleotide polymorphisms (SNPs) that lead to mutations of V600N599 would provide important information about the diagnosis and prognosis of cancer.

In addition to providing information about cancer diagnosis and prognosis, the ability to detect SNPs that lead to mutations of V600/V599 also would provide important information about the therapeutic efficacy of drugs targeting the MAPK pathway. Detection of a mutation in codon 600 of BRAF, such as V600E by amplification of a polynucleotide sequence comprising V600E, reportedly enables the determination of the sensitivity of cancer cells to a B-raf kinase inhibitor (see U.S. Pat. App. Pub. Nos. 2010/0173294 and 2011/0212991). Detection of homozygous/heterozygous V600E or V600D genotype or any genotype characterized by BRAF gain-of-function phenotype reportedly enables evaluation of sensitivity of malignant/neoplastic cells to ERK1/ERK2/MEK inhibitors (see U.S. Pat. App. Pub. No. 2011/0158944; see also Int'l Pat. App. Pub. No. WO 2009/073513). The detection of a mutation in BRAF, such as V600E, reportedly enables the generation of a personalized report for treatment of a patient with colon cancer with cetuximab or panitumumab (see U.S. Pat. App. Pub. No. 2011/0230360). Shinozaki, et al., Clin. Cancer Res. 13: 2068-2074 (2007), discloses the analysis of circulating B-RAF DNA mutations in serum for monitoring melanoma patients receiving biochemotherapy. Methods of optimizing treatment of cancer based on BRAF mutations, as well as other methods, are described in Int'l Pat. App. Pub. No. WO 2011/106298.

Existing methods for detecting BRAF mutations, such as sequencing, pyrosequencing, array, shifted termination assay (STA), polymerase chain reaction (PCR) followed by dual-priming oligonucleotide (DPO) PCR, and real-time PCR utilizing either allele-specific primers or allele-specific detectable oligonucleotide are accompanied by various disadvantages (see, e.g., Benlloch, et al., J. Mol. Diagn. 8: 540-543 (2006), for comparison of automatic sequencing and real-time chemistry methodology in the detection of BRAF V600E mutation in colorectal cancer; see, e.g., Hay, et al., Arch. Pathol. Lab. Med. 131: 1361-1367 (2007), for melting curve analysis of PCR products used to identify BRAF mutations in melanocytic lesions and papillary thyroid carcinoma samples; see, e.g., Jarry, et al., Mol. Cell. Detectable oligonucleotides 18: 349-352 (2004), for real-time allele-specific amplification in the detection of BRAF V600E; see, e.g., Sapio, et al., Eur. J. Endocrinol. 154: 341-348 (2006), for use of mutant allele-specific PCR amplification (MASA) to detect BRAF mutation in thyroid papillary carcinoma; and, see, e.g., Turner, et al., J. Cutan. Pathol. 32: 334-339 (2005), for use of the ligase detection reaction to detect BRAF V600E in melanocytic lesions). Sequencing and pyrosequencing methods are limited by their sensitivity, with the lowest detectable mutant content around 10-20% (% mutant over total background). Other methods, such as real-time PCR utilizing allele-specific detectable oligonucleotides, STA, array, and PCR/DPO are also limited by their sensitivity. Ideally, a sensitivity of 1% or better is desired.

Existing methods that lack sufficient specificity, such as real-time PCR, cannot differentiate between specific types of mutations, such as V600E and V600K. Even though V600E accounts for 90% of all mutations found at this amino acid position, other amino acid substitutions with clinical significant have been found in various cancers, sometimes with high prevalence, such as V600K in melanoma. Thus, the ability to differentiate between specific types of mutations is becoming increasingly important.

Assay workflow and automation are critical aspects of any diagnostic method. For certain technologies, such as sequencing, existing assay procedures are long and complicated. Other technologies, such as PCR/DPO (dual priming oligo) and array-based methods, may require extensive sample handling post-PCR, which is prone to amplicon contamination. In certain cases, additional steps have to be included in order to achieve differentiated detection of multiple mutations.

The present disclosure seeks to overcome some of the disadvantages attendant currently available methods of detecting germ-line and somatic mutations, especially those associated with hereditary abnormalities, disease progression and therapeutic efficacy. This and other objects and advantages, as well as inventive features, will be apparent from the detailed description provided herein.

SUMMARY

The present invention is that the SNPs are maintained in the context of amino acid substitutions because it is the mutated protein that is directly involved in the biological abnormality. Another insight is that the SNPs themselves are directly involved in the process of gene regulation, such as disruption of a splicing event. It is also possible that some of the SNPs have no obvious or known impact on biological functions but are co-localized with the SNPs of interest in the primary nucleotide sequence.

Thus, the present invention is directed towards compositions and methods suitable for the improved detection of SNPs (i.e., target SNPs). The improved detection of SNPs afforded by the present invention is based on the novel and non-obvious discovery of a new approach to primer design. The primer designs suitable for the detection of SNPs (as discussed, infra) are summarized in FIGS. 2 and 3. It is noted here that the common feature to all designs is the introduction of one or more additional mismatched bases 5' to the naturally occurring mismatches to allow for allele specific priming. The rationale for this design feature is as follows: The naturally occurring mismatches can sometimes be tolerated by polymerase depending upon the content, number and position(s) of the mismatch(es). The introduced additional mismatch(es) are designed to further reduce PCR efficiency for the non-specific targets without significantly impacting the specific targets. As a result, the targets with the mutations of interest will be amplified efficiently while non-specific targets will not due to the presence of 2 or more mismatched at or near the 3' end of the primers. This design feature can be applied to either the forward or reverse primer to enable the allele specific priming. As described in FIGS. 2 and 3, such a design may already be sufficient to achieve allele specific detection and/or identification. Depending on the actual SNP pattern, e.g., in cases where two individual SNPs are far apart, it may be feasible to detect specific SNPs if both the forward and reverse primers are designed to be allele specific (see, FIG. 5). In addition to the SNPs of interest, there might be other existing SNPs nearby that are not clinically relevant and need to be tolerated by the assay. One solution is to design degenerate bases at those positions (see, FIG. 2, example 2) or other modified nucleotide bases allowing indiscriminate binding.

The design principles and strategies described above and exemplified below can be adopted for use with codon-based AS-PCR to detect single amino acid mutations. In the genetic codon table, every amino acid including the stop codon (TGA/UGA) is encoded by a different array of three nucleotides. In order to minimize non-specific signals from other amino acid mutations and/or nominal sequences that can potentially be present in a sample, the SNPs region for the whole codon need to be included in the primer design. In order to detect multiple codons corresponding to one amino acid mutation of interest (depending on the specific amino acid) or multiple amino acid mutations, multiple allele specific primers are used (as a pool or separately), each carrying a 3' end sequence that is specific to one of the codons of interest. These allele specific primers have a perfect match with their intended targets at the last 3 nucleotides of the 3' terminus but will have at least one mismatch in the same region when compared with any other codon. As discussed above, one mismatch among the last 3 nucleotides of a primer can sometimes by tolerated by the polymerase; hence one additional mismatch in introduced at a nucleotide position 5' to the codons of interest to further reduce PCR efficiency for the no-specific target without significantly impacting the specific targets. As a result, the targets with only the amino acid mutations of interest will be amplifies while other non-specific target(s) will not due to the presence of 2 or more mismatches at or near the 3' end of the primer. This strategy not only covers all possible genetic variations that encode the amino acid of interest but also eliminates the non-specific signals from all other potential amino acids (from either mutated or wild-type sequences).

One of ordinary skill in the art would, from the teachings of the present specification, be able to design primers for use in SNP detection for any desired target. One exemplification below teaches a method of detecting at least one mutation (X) of the codon encoding valine at amino acid position 600 (V600X) in exon 15 of the BRAF gene in a sample of nucleic acid from a human is provided. The method comprises:

(a) performing an amplification reaction with the sample of nucleic acid, wherein the amplification reaction comprises a primer, the last three nucleotides at the 3' terminus of which encodes X and wherein the fourth nucleotide from the 3' terminus contains a base other than adenine (A), wherein, if X is present, the primer anneals to X, wherein, if the sample of nucleic acid is mRNA, step (a) further comprises obtaining cDNA reverse-transcribed from the mRNA or reverse-transcribing cDNA from the mRNA before performing the amplification reaction, whereupon, if X is present, the amplification reaction produces an amplification product comprising X, (b) detecting the amplification product comprising X, and wherein, if X is encoded by more than one codon, the amplification reaction comprises a primer for each codon. The amplification reaction can further comprise at least one peptide nucleic acid (PNA) clamp, wherein at least one PNA clamp is wild-type and, if the amplification reaction comprises one or more other PNA clamps, the PNA clamps a detectable oligonucleotide and/or a primer, the PNA clamps a detectable oligonucleotide and/or a primer by binding an unwanted target and preventing a primer from amplifying from an unwanted target. Detecting the amplification product comprising X can comprise detecting a labeled primer or contacting the amplification product with a detectable oligonucleotide and detecting hybridization of the detectable oligonucleotide to the amplification product comprising X. The amplification reaction can further comprise an internal control primer, in which case the amplification reaction also produces an amplification product comprising the internal control, in which case step (b) includes detecting the amplification product comprising the internal control. Detecting the amplification product comprising the internal control can comprise detecting a labeled primer or contacting the amplification product with a detectable oligonucleotide and detecting hybridization of the detectable oligonucleotide to the amplification product comprising the internal control. X is at least one amino acid selected from the group consisting of E, K, D, R, and N. For example, X can be at least one amino acid selected from the group consisting of E, K, and D. X can be E, E and K, E and D, K and D, or E, K, and D. When the method comprises detecting two or more X, the method can comprise performing an amplification reaction with the sample of DNA for each X together or separately. In this regard, the method also can further comprise determining which X is present in the sample of nucleic acid.

The present invention is also directed to set of primers for amplification of V600X in exon 15 of the BRAF gene in a sample of nucleic acid from a human is also provided. The set of primers comprises at least one primer selected from the group consisting of:

(a) an oligonucleotide comprising the nucleotide sequence GGTCTAGCTACNGAA [SEQ ID NO: 59] at its 3' terminus and/or an oligonucleotide comprising the nucleotide sequence GGTCTAGCTACNGAG [SEQ ID NO: 60] at its 3' terminus, (b) an oligonucleotide comprising the nucleotide sequence GGTCTAGCTACNAAA [SEQ ID NO: 46] at its 3' terminus and/or an oligonucleotide comprising the nucleotide sequence GGTCTAGCTACNAAG [SEQ ID NO: 47] at its 3' terminus, (c) an oligonucleotide comprising the nucleotide sequence GGTCTAGCTACNGAT [SEQ ID NO: 48] at its 3' terminus and/or an oligonucleotide comprising the nucleotide sequence GGTCTAGCTACNGAC [SEQ ID NO: 49] at its 3' terminus, (d) an oligonucleotide comprising the nucleotide sequence GGTCTAGCTACNAAT [SEQ ID NO: 50] at its 3' terminus and/or an oligonucleotide comprising the nucleotide sequence GGTCTAGCTACNAAC [SEQ ID NO: 51] at its 3' terminus, (e) an oligonucleotide comprising the nucleotide sequence GGTCTAGCTACNCGT [SEQ ID NO: 52] at its 3' terminus, an oligonucleotide comprising the nucleotide sequence GGTCTAGCTACNCGC [SEQ ID NO: 53] at its 3' terminus, an oligonucleotide comprising the nucleotide sequence GGTCTAGCTACNCGA [SEQ ID NO: 54] at its 3' terminus, an oligonucleotide comprising the nucleotide sequence GGTCTAGCTACNCGG [SEQ ID NO: 55] at its 3' terminus, an oligonucleotide comprising the nucleotide sequence GGTCTAGCTACN AGA [SEQ ID NO: 56] at its 3' terminus, and an oligonucleotide comprising the nucleotide sequence GGTCTAGCTACNAGG [SEQ ID NO: 57] at its 3' terminus, (d) and (e),
(a) and (b),
(a) and (c),
(b) and (c),
(a), (b), and (c),
any of (a), (b), and (c), in further combination with (d),
any of (a), (b), and (c), in further combination with (e), and
any of (a), (b), and (c), in further combination with (d) and (e), wherein N is a nucleotide containing a base other than adenine (A), and wherein the oligonucleotide comprises from about 15 nucleotides to about 35 nucleotides. The oligonucleotide can further comprise contiguous with the G at the 5' end of the nucleotide sequence one or more contiguous nucleotides of the nucleotide sequence 5' AATAGGTGATTTT 3' [SEQ ID NO: 58] starting with the T at the 3' end of the nucleotide sequence. The set of primers can further comprise a primer, such as a reverse primer, comprising from about 15 nucleotides to about 35 nucleotides, wherein, when the primer comprises 15-27 nucleotides, it comprises 15-27 contiguous nucleotides of SEQ ID NO: 10. The detectable oligonucleotide can comprise from about 15 nucleotides to about 35 nucleotides, wherein, when the detectable oligonucleotide comprises 15-20 nucleotides, it comprises 15-20 contiguous nucleotides of SEQ ID NO: 11.

A kit is also provided. The kit comprises:

(i) a set of primers for detection of V600X in exon 15 of the BRAF gene in a sample of nucleic acid from a human, wherein the set of primers comprises at least one primer selected from the group consisting of:

(a) an oligonucleotide comprising the nucleotide sequence GGTCTAGCTACNGAA [SEQ ID NO: 59] at its 3' terminus and/or an oligonucleotide comprising the nucleotide sequence GGTCTAGCTACNGAG [SEQ ID NO: 60] at its 3' terminus, (b) an oligonucleotide comprising the nucleotide sequence GGTCTAGCTACNAAA [SEQ ID NO: 46] at its 3' terminus and/or an oligonucleotide comprising the nucleotide sequence GGTCTAGCTACNAAG [SEQ ID NO: 47] at its 3' terminus, (c) an oligonucleotide comprising the nucleotide sequence GGTCTAGCTACNGAT [SEQ ID NO: 48] at its 3' terminus and/or an oligonucleotide comprising the nucleotide sequence GGTCTAGCTACNGAC [SEQ ID NO: 49] at its 3' terminus, (d) an oligonucleotide comprising the nucleotide sequence GGTCTAGCTACNAAT [SEQ ID NO: 50] at its 3' terminus and/or an oligonucleotide comprising the nucleotide sequence GGTCTAGCTACNAAC [SEQ ID NO: 51] at its 3' terminus, (e) an oligonucleotide comprising the nucleotide sequence GGTCTAGCTACNCGT [SEQ ID NO: 52] at its 3' terminus, an oligonucleotide comprising the nucleotide sequence GGTCTAGCTACNCGC [SEQ ID NO: 53] at its 3' terminus, an oligonucleotide comprising the nucleotide sequence GGTCTAGCTACNCGA [SEQ ID NO: 54] at its 3' terminus, an oligonucleotide comprising the nucleotide sequence GGTCTAGCTACNCGG [SEQ ID NO: 55] at its 3' terminus, an oligonucleotide comprising the nucleotide sequence GGTCTAGCTACN AGA [SEQ ID NO: 56] at its 3' terminus, and an oligonucleotide comprising the nucleotide sequence GGTCTAGCTACNAGG [SEQ ID NO: 57] at its 3' terminus, (d) and (e),
(a) and (b),
(a) and (c),
(b) and (c),
(a), (b), and (c),
any of (a), (b), and (c), in further combination with (d),
any of (a), (b), and (c), in further combination with (e), and
any of (a), (b), and (c), in further combination with (d) and (e), wherein N is a nucleotide containing a base other than adenine (A), and wherein the oligonucleotide comprises from about 15 nucleotides to about 35 nucleotides, and (ii) instructions for a method of detecting at least one mutation (X) of the codon encoding valine at amino acid position 600 (V600X) in exon 15 of the BRAF gene in a sample of nucleic acid from a human, which method comprises:

(a) performing an amplification reaction with the sample of nucleic acid, wherein the amplification reaction comprises a primer, the last three nucleotides at the 3' terminus of which encodes X and wherein the fourth nucleotide from the 3' terminus contains a base other than adenine (A), wherein, if X is present, the primer anneals to X, and at least one peptide nucleic acid (PNA) clamp, wherein at least one PNA clamp blocks the amplification from wild-type target, wherein, if the sample of nucleic acid is mRNA, step (a) further comprises obtaining cDNA reverse-transcribed from the mRNA or reverse-transcribing cDNA from the mRNA before performing the amplification reaction, whereupon, if X is present, the amplification reaction produces an amplification product comprising X, and (b) detecting the amplification product comprising X, wherein, if X is encoded by more than one codon, the amplification reaction comprises a primer for each codon, wherein, if the method comprises detecting two or more X, the method can comprise performing an amplification reaction with the sample of nucleic acid for each X together or separately, and wherein the method also can further comprise determining which X is present in the sample of nucleic acid. The oligonucleotide can further comprise contiguous with the G at the 5' end of the nucleotide sequence one or more contiguous nucleotides of the nucleotide sequence 5' AATAGGTGATTTT 3' [SEQ ID NO: 58] starting with the T at the 3' end of the nucleotide sequence. The kit can further comprise a primer, such as a reverse primer, comprising from about 15 nucleotides to about 35 nucleotides, wherein, when the primer comprises 15-27 nucleotides, it comprises 15-27 contiguous nucleotides of SEQ ID NO: 10. The kit can further comprise a detectable oligonucleotide comprising from about 15 nucleotides to about 35 nucleotides, wherein, when the detectable oligonucleotide comprises 15-20 nucleotides, it comprises 15-20 contiguous nucleotides of SEQ ID NO: 11. X can be at least one amino acid selected from the group consisting of E, K, D, R, and N. X can be at least one amino acid selected from the group consisting of E, K, and D, such as E, E and K, E and D, K and D, or E, K, and D.

The present invention is not limited to the detection of BRAF mutations and one of ordinary skill in the art, based on the teachings of the present specification, would be able to design primers and assays for the detection of any desired target SNP. Thus, the present invention is also directed towards a method of detecting at least one mutation (X) of a codon in a gene in a sample of nucleic acid is also provided. The method comprises:

(a) performing an amplification reaction with the sample of nucleic acid, wherein the amplification reaction comprises a primer, the last three nucleotides at the 3' terminus of which encodes X and wherein the fourth nucleotide from the 3' terminus contains a base other than adenine (A), wherein, if X is present, the primer anneals to X, wherein, if the sample of nucleic acid is mRNA, step (a) further comprises obtaining cDNA reverse-transcribed from the mRNA or reverse-transcribing cDNA from the mRNA before performing the amplification reaction, whereupon, if X is present, the amplification reaction produces an amplification product comprising X, (b) detecting the amplification product comprising X, and wherein, if X is encoded by more than one codon, the amplification reaction comprises a primer for each codon. The amplification reaction can further comprise at least one peptide nucleic acid (PNA) clamp, wherein at least one PNA clamp blocks the amplification from wild-type target, and wherein, if the amplification reaction comprises one or more other PNA clamps, the PNA preferably clamps a detectable oligonucleotide and/or a primer. Detecting the amplification product comprising X can comprise detecting a labeled primer or contacting the amplification product with a detectable oligonucleotide and detecting hybridization of the detectable oligonucleotide to the amplification product comprising X. The amplification reaction can further comprise an internal control primer, in which case the amplification reaction also produces an amplification product comprising the internal control, in which case step (b) includes detecting the amplification product comprising the internal control. Detecting the amplification product comprising the internal control can comprise detecting a labeled primer or contacting the amplification product with a detectable oligonucleotide and detecting hybridization of the detectable oligonucleotide to the amplification product comprising the internal control. When the method comprises detecting two or more X, the method can comprise performing an amplification reaction with the sample of nucleic acid for each X together or separately. In this regard, the method also can further comprise determining which X is present in the sample of nucleic acid.

A method of designing a primer for detection of at least one mutation (X) of a codon in a gene in a sample of nucleic acid is also provided. The method comprises synthesizing a primer, the last three nucleotides at the 3' terminus of which encodes X and wherein the fourth nucleotide from the 3' terminus contains a base other than that which is present in the wild-type gene, whereupon a primer for detection of at least one mutation (X) in a codon in a gene in a sample of nucleic acid is designed.

The present invention is also directed towards a dual allele specific primer design strategy. In situations where there are multiple SNPs of interest in multiple positions, with one SNP per position, for example, the simultaneous presence of multiple SNPs in a given sample will be detected. The single SNP should not be detected. An exemplification of the dual allele specific primer design strategy is given in FIG. 5. In this regard, the primer design exemplified in FIG. 2 can be applied to either the forward or the reverse primer in the dual allele specific primer design method of the present invention.

The present invention also contemplates a method for detecting a sequence of nucleic acid comprising a target single nucleotide polymorphism (SNP) of interest (the first SNP of interest), said method comprising: a) providing i) a sequence of nucleic acid suspected of containing the target SNP, ii) a primer that is complementary to the sequence comprising the target SNP, wherein the base located three bases 5' from a primer nucleotide that is complementary to the target SNP is a base that is not complementary to the corresponding base of the nucleic acid comprising the target SNP sequence, thereby creating in the primer a mismatched base; b) contacting the sample suspected of containing the target SNP with the primer under conditions that permit the binding of the primer to the target SNP, if present, to create a bound target SNP; and c) detecting the bound target SNP. The present invention also contemplates that wherein if the sample of nucleic acid is mRNA, step b) further comprises obtaining cDNA reverse-transcribed from the mRNA or reverse-transcribing cDNA from the mRNA.

The present invention also contemplates that when the sequence of nucleic acid comprises more than one SNP (the second SNP of interest), a separate primer is used to detect the second SNP of interest.

The present invention also contemplates that when the sequence of nucleic acid comprising the target SNP of interest comprises one or more non-target mutations, the primer contains nucleotides complementary to said one or more non-target mutations.

The present invention also contemplates that when the sequence of nucleic acid comprising the target SNP of interest (the first SNP of interest) contains one or more additional target SNPs of interest at the same sequence position that the method additionally comprises a primer containing a base complementary to each additional one or more SNPs of interest.

The present invention also contemplates that when the sequence of nucleic acid comprising the target SNP of interest (the first SNP of interest) contains one or more additional target SNPs of interest at a sequence location or locations that differ from the sequence location of the first SNP of interest, the primer additionally comprises a base or bases complementary to the one of more additional SNPs of interest.

The present invention also contemplates a method for detecting a sequence of nucleic acid comprising one or more target single nucleotide polymorphisms (SNP) of interest, wherein the SNPs are located at one or more positions on the sequence of nucleic acid, the method comprising: a) providing, i) a sequence of nucleic acid suspected of containing the one or more target SNPs such that the first sequence containing one or more SNPs is the first sequence and such that the most 5' SNP is the first target SNP, a second sequence containing one of more SNPs wherein at least one SNP differs from the one or more SNPs of the first sequence, is the second sequence and such that the most 5' SNP is the first target SNP, etc., ii) a primer complementary to each sequence comprising the one or more target SNPs wherein for each primer the base located three bases 5' from a primer nucleotide that is complementary to the first target SNP is a base that is not complementary to the corresponding base of the nucleic acid comprising the target SNP sequence, thereby creating in the primer a first mismatched base; b) contacting the sample suspected of containing the sequences containing the one or more target SNPs with the primer or primers under conditions that permit the binding of the primer or primers to the one or more target SNPs, if present, to create a bound target SNPs; and c) detecting the bound target SNPs. The present invention also contemplates that wherein if the sample of nucleic acid is mRNA, step b) further comprises obtaining cDNA reverse-transcribed from the mRNA or reverse-transcribing cDNA from the mRNA.

The present invention also contemplates a dual allele specific primer strategy (see, FIG. 5) wherein both forward and reverse primers are created for the detection of multiple target SNPs in a nucleotide sequence.

BRIEF DESCRIPTION OF THE FIGURES

FIG. 1 illustrates the design of primers, wherein the V600 codon is underlined.

FIG. 2 shows multiple primer design strategies of the present invention.

FIG. 3 shows a schematic diagram illustrating the design principle for amino acid specific primers using BRAF V600E as a model target.

FIG. 4 shows amino acid specific primer design for BRAF V600E as a model target.

FIG. 5 shows the dual allele specific primer design strategy of the present invention.

FIGS. 6 A & B show a comparison of two different primer designs for BRAF V600E detection. Also shown are the number of mismatched bases in each primer design. FIG. 6A discloses SEQ ID NOS 1, 2, 61, and 22, respectively, in order of appearance.

FIGS. 7 A & B show a comparison of two different primer designs for BRAF V600E detection presented as (A) CT and (B) PCR curves.

FIG. 8 shows the results of SNP detection using primers specific for either V600E or V600K.

DETAILED DESCRIPTION

The present disclosure is predicated, at least in part, on oligonucleotide primers and detectable oligonucleotides for the real-time amplification and detection of a single or multiple nucleotide polymorphisms (SNP). The detection of the SNP at amino acid position 600 of BRAF is an example. This SNP can result in substitution of valine with glutamic acid (designated herein as V600E), lysine (designated herein as V600K), aspartic acid (V600D), arginine (V600R), or asparagine (V600N), for example. Since mutation of valine at amino acid position 600 to glutamic acid, lysine, and/or aspartic acid accounts for more than 90% of all BRAF mutations, the primers and detectable oligonucleotides provided herein enable, among other things, cancer prognosis and assessment of therapeutic efficacy of a drug targeting the MAPK pathway.

Allele-specific amplification and polymerase chain reaction (PCR) clamping are combined to detect the SNP. The combination enables sensitivity lower than or equal to about 0.5% mutant content with excellent specificity.

The following definitions are relevant to the present disclosure:

(a) "About" refers to approximately a +/−10% variation from the stated value. It is to be understood that such a variation is always included in any given value provided herein, whether or not specific reference is made to it.

(b) "Allele-specific primer" in the context of the present disclosure refers to a primer (see "primer") that hybridizes to a target sequence such that the 3' end, usually the 3' nucleotide, of the primer aligns with a site of interest, e.g., nucleotide 1800, which is the third nucleotide in codon 600 of BRAF, and is exactly complementary to either the wild-type allele or a mutant allele at the codon of the SNP. The use of an allele-specific primer enables discrimination between alleles based on differential formation of extension products during nucleic acid, e.g., DNA, amplification.

(c) "Detectable oligonucleotide" refers to an oligonucleotide that selectively hybridizes to a target nucleic acid under suitable conditions and can be detected.

(d) "High-affinity nucleic acid analogue" refers to a modified nucleic acid that hybridizes to a complementary nucleic acid, such as a deoxyribonucleic acid (DNA), with higher affinity than an unmodified nucleic acid having the same base sequence. High-affinity nucleic acids include, but are not limited to, locked nucleic acids (LNAs), peptide nucleic acids (PNAs), hexitol nucleic acids (HNAs), phosphoramidates, and the like.

(e) "Hybridization" refers to the formation of a duplex structure by complementary base pairing between two single-stranded nucleic acids. Hybridization can occur between exactly complementary nucleic acid strands or between complementary nucleic acid strands that contain a low number of mismatches.

(f) "Locked nucleic acid (LNA)" refers to a nucleic acid analogue (a polymer of purine and/or pyrimidine bases) characterized by the presence of one or more monomers that are conformationally restricted nucleotide analogues with an extra 2H—O, 4H—C-methylene bridge added to the ribose ring. LNA has been defined as an oligonucleotide having one or more 2H—O, 4H—C-methylene-(D-ribofuranosyl) nucleotide monomers. LNAs are resistant to exonucleases and heat.

(g) "Nucleic acid," "polynucleotide," and "oligonucleotide" refer to primers, detectable oligonucleotides, and oligomers, irrespective of length, and include polydeoxyribonucleotides, polyribonucleotides, and any other N-glycoside of a modified/unmodified, purine/pyrmidine base. Examples include single-stranded DNA (ssDNA), double-stranded DNA (dsDNA), single-stranded RNA (ssRNA), and double-stranded RNA (dsRNA). Such molecules can comprise phosphodiester linkages or modified linkages including, but not limited to, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations thereof. Such molecules can comprise adenine, guanine, thymine, cytosine and/or uracil, as well as other modified, non-standard, or derivatized bases. Alternatively or additionally, such molecules can comprise one or more modified sugar moieties.

(h) "Peptide nucleic acid (PNA)" refers to a synthetic DNA analog in which the normal phosphodiester backbone is replaced with a N-(2-aminoethyl)glycine chain. Its nucleobases complement DNA or RNA in the same A-T(U) and G-C manner (Nielsen, et al., Science 254: 1497-1500 (1991); Hanvey, et al., Science 258: 1481-1485 (1992); and Egholm, et al., Nature 365: 566-568 (1993)). The artificial backbone renders PNA resistant to nucleases. PNA can be synthesized in accordance with methods known in the art (see, e.g., Hyrup, et al., Bioorg. Med. Chem. 4: 5-23 (1996); Int'l Pat. App. Pub. Nos. WO 92/20702 and 92/20703; and U.S. Pat. No. 5,539,082, the contents of all of which are incorporated herein by reference for their teachings regarding same). Two important features make PNA a superior PCR clamp for specific alleles. It cannot serve as a primer for polymerization. It cannot serve as a substrate for exonuclease activity by Taq polymerase. In addition, the melting temperature of a perfectly matched PNA-DNA duplex is higher than that of a DNA-DNA duplex of the same length; thus, the PNA-DNA duplex is more stable. A single mismatch in a PNA-DNA hybrid will cause a drop in the melting temperature of about 10-18° C. (Kyger, et al., Anal. Biochem. 260: 142-148 (1998)). Therefore, over an appropriate temperature range PNA can specifically block primer/detectable oligonucleotide annealing or chain elongation on a perfectly matched template without interfering with reactions on templates with mismatched base(s) (Sun, et al., Nat. Biotechnol. 20: 186-189 (2002); Thiede, et al., Nucleic Acids Res. 24: 983-984 (1996); and Taback, et al., Int. J. Cancer 111: 409-414 (2004)), which is referred to as PNA-mediated PCR clamping (Orum, et al., Nucleic Acids Res. 21: 5332-5336 (1993)). The large difference in melting temperature between perfectly matched and mismatched hybrids makes PNA a good sensor of point mutations (see, e.g., Karadag, et al., Nucleic Acids Res. 32: e63 (2004); Taback, et al. (2004), supra; Hancock, et al., Clin. Chem. 48: 2155-2163 (2002); Takiya, et al., Biosci. Biotechnol. Biochem. 68: 360-368 (2004); Kirishima, et al., J. Hepatol. 37: 259-265 (2002); and Ohishi, et al., J. Med. Virol. 72: 558-565 (2004)). U.S. Pat. App. Pub. No. 2004/0014105 discloses methods for the selective enrichment of polynucleotides that are present in a sample in low abundance. The method uses enzymatically non-extendable nucleobase oligomer (e.g., PNA) as a PCR clamp to block selectively polymerase activity on polynucleotides that are present in the sample in high abundance, thereby resulting in an enrichment of less abundant species in the sample. "PNA" may include a PNA clamp. Clamping operates by physical competition between a PNA and a DNA primer or probe for a common target site, thereby interfering with primer elongation.

(i) "Polymerase chain reaction (PCR)" is a method of making copies of a DNA sequence. The method employs thermal cycling (i.e., cycles of heating and cooling for denaturation (or melting) and replication of the DNA, respectively). Primers, which are short DNA fragments containing sequences complementary to the DNA sequence to be copied, and a heat-stable DNA polymerase, such as the one from *Thermus aquaticus*, which is referred to as Taq polymerase, are used to select the DNA sequence and copy it (see, e.g., U.S. Pat. Nos. 4,683,195; 4,800,195, and 4,965,188, all of which are incorporated by reference herein for their teachings regarding same). With repeated cycling the copies, which are made, are used as templates for generating further copies (i.e., a chain reaction). PCR techniques include, but are not limited to, standard PCR, allele-specific PCR, assembly PCR, asymmetric PCR, digital PCR, Hot-start PCR, intersequence-specific PCR, inverse PCR, ligation-mediated PCR, methylation-specific PCR, miniprimer PCR, nested PCR, overlap-extension PCR, real-time PCR, reverse transcription-PCR, solid phase PCR, thermal asymmetric interlaced PCR, and Touchdown PCR.

(j) "Primer" as used herein refers to an oligonucleotide that initiates template-dependent nucleic acid synthesis. In the presence of a nucleic acid template, nucleoside triphosphate precursors, a polymerase, and cofactors, under suitable conditions of temperature and pH, the primer can be extended at its 3' terminus by the addition of nucleotides by the polymerase to yield a primer extension product. The primer may vary in length depending on the particular conditions employed and the purpose of the amplification. For example, a primer for amplification for a diagnostic purpose is typically from about 15 to about 35 nucleotides in length. The primer must be of sufficient complementarity to the desired template to prime the synthesis of the desired extension product. In other words, the primer must be able to anneal with the desired template strand in a manner sufficient to provide the 3' hydroxyl moiety of the primer in appropriate juxtaposition for use in the initiation of synthesis by a polymerase. It is not necessary for the primer to be an exact complement of the desired template. For example, a non-complementary nucleotide sequence can be present at the 5' end of an otherwise complementary primer. Alternatively, non-complementary bases can be interspersed within the oligonucleotide primer, provided that the primer sequence has sufficient complementarity with the sequence of the desired template strand to provide a template-primer complex for the synthesis of the extension product.

(k) "Specifically hybridize(s)," as used herein, refers to the ability of a given nucleic acid, such as a primer or detectable oligonucleotide, to bind specifically to another nucleic acid.

(l) "Stringent" or "sequence-specific" hybridization conditions refers to conditions under which exactly complementary nucleic acid strand will preferentially hybridize. Stringent hybridization conditions are well-known in the art. Stringent conditions are sequence-dependent and will be different under different circumstances. Generally, stringent conditions are selected to be about 5° C. lower than the thermal melting point ($T_m$) for the specific sequence under defined conditions of pH and ionic strength at which 50% of the base pairs are dissociated.

(m) "Substantially complementary" refers to sequences that are complementary except for minor regions of mismatches. Typically, the total number of mismatches in a nucleic acid that is about 15 nucleotides in length is about 3 nucleotides or less.

(n) "Target sequence" and "target region" refer to a region of a nucleic acid that it to be detected, or detected and analyzed, and comprises the polymorphic site of interest, i.e., V600D, V600E, V600K, V600N, or V600R in the context of the present disclosure.

(o) "V600D" refers to a TG→AT or TG→AC mutation starting at nucleotide position 1799 of BRAF that results in substitution of aspartic acid for valine.

(p) "V600E" refers to a T→A or TG→AA mutation starting at nucleotide position 1799 of BRAF that results in substitution of glutamic acid for valine. V600E is also known as V599E (T→A mutation at nucleotide position 1796 of BRAF) under a previous numbering system (Kumar, et al., Clin. Cancer Res. 9: 3362-3368 (2003)).

(q) "V600K" refers to a GT→AA or GTG→AAA mutation starting at nucleotide position 1798 of BRAF that results in substitution of lysine for valine.

(r) "V600N" refers to a GTG→AAT or GTG→AAC mutation starting at nucleotide position 1798 of BRAF that results in substitution of asparagine for valine.

(s) "V600R" refers to a GT→AG, GT→CG, GTG→AGA, GTG→CGT, GTG→CGC, or GTG→CGA mutation starting at nucleotide position 1798 of BRAF that results in substitution of arginine for valine.

The terminology used herein is for the purpose of describing particular embodiments only and is not otherwise intended to be limiting.

Method of Detection

A method of detecting at least one mutation (X) of the codon encoding, for example, valine at amino acid position 600 (V600X) in exon 15 of the BRAF gene, in a sample of nucleic acid from a subject (e.g., a human subject) is provided. The method comprises:

(a) performing an amplification reaction with the sample of nucleic acid, wherein the amplification reaction comprises a primer, the last three nucleotides at the 3' terminus of which encodes X and wherein the fourth nucleotide from the 3' terminus contains a base other than adenine (A), wherein, if X is present, the primer anneals to x, wherein, if the sample of nucleic acid is mRNA, step (a) further comprises obtaining cDNA reverse-transcribed from the mRNA or reverse-transcribing cDNA from the mRNA before performing the amplification reaction, whereupon, if X is present, the amplification reaction produces an amplification product comprising X, (b) detecting the amplification product comprising X, and wherein, if X is encoded by more than one codon, the amplification reaction comprises a primer for each codon. With regard to a primer, reference is made herein to the nucleotides (nt) at the 3' terminus as follows:

nt--nt--nt--nt 3'

Position: 4th 3rd 2nd 1st.

The amplification reaction can further comprise at least one peptide nucleic acid (PNA) clamp, wherein at least one PNA clamp blocks the amplification from wild-type target, and wherein, if the amplification reaction comprises one or more other PNA clamps, the PNA preferably clamps a detectable oligonucleotide and/or a primer by binding an unwanted target and prevents a primer from amplifying from an unwanted target. Detecting the amplification product comprising X can comprise detecting a labeled primer or contacting the amplification product with a detectable oligonucleotide and detecting hybridization of the detectable oligonucleotide to the amplification product comprising X. The amplification reaction can further comprise an internal control primer, in which case the amplification reaction also produces an amplification product comprising the internal control, in which case step (b) includes detecting the amplification product comprising the internal control. Detecting the amplification product comprising the internal control can comprise detecting a labeled primer or contacting the amplification product with a detectable oligonucleotide and detecting hybridization of the detectable oligonucleotide to the amplification product comprising the internal control. X is at least one amino acid selected from the group consisting of E, K, D, R, and N. For example, X can be at least one amino acid selected from the group consisting of E, K, and D. X can be E, E and K, E and D, K and D, or E, K, and D. X also can be another amino acid besides E, K, D, R, or N, including V encoded by a codon other than that which is found in wild-type (i.e., a silent mutation), or a premature stop codon. Preferably, however, X is at least one of E, K, D, R, or N as indicated.

When the method comprises detecting two or more X, the method can comprise performing an amplification reaction with the sample of nucleic acid for each X together or separately. In this regard, the method also can further comprise determining which X is present in the sample of nucleic acid.

The amplification reaction can, and preferably does, comprise an internal control (IC) nucleic acid and a pair of primers for amplifying the IC nucleic acid. When the amplification reaction comprises an IC nucleic acid, the conditions that promote amplification also promote amplification of the IC nucleic acid.

Thus, primer selection enables detection of at least one mutation in accordance with the present disclosure. This is in distinct contrast to methods of the prior art in which detectable oligonucleotide selection enables detection of a mutation. The present method is also specific for mutation at the amino acid level (i.e., primers are selected to amplify all codons encoding a particular amino acid but no other amino acid). This is in distinct contrast to methods of the prior art, which are specific for nucleic acids and detect multiple amino acids encoded by codons in which the nucleotides at the first and second positions of the codon are the same. Furthermore, the present method can be performed on DNA or RNA, is inherently quantitative, and can be adapted for detection of SNPs in other locations in the same gene as well as SNPs in other genes.

Any suitable sample of a tissue or a body fluid can be used as the source of the sample of nucleic acid, i.e., DNA or RNA. Typically, the source is a tumor or cells/tissues from a metastatic site or blood (or component thereof). Blood, plasma, serum, lymph, and tumor biopsies, for example, can be used. Other samples include urine, cerebrospinal fluid, pleural fluid, sputum, peritoneal fluid, bladder washings, secretions (e.g., breast), oral washings, touch preparations, and fine-needle aspirates. A plasma or whole blood can be preserved, such as by the addition of a chelating agent, e.g., ethylenediaminetetraacetic acid (EDTA) or a salt thereof, such as a disodium salt or a calcium disodium salt. A proteinase, such as proteinase K, can be added to the sample to digest unwanted proteins.

Tissue samples can be generally preserved as formalin-fixed, paraffin-embedded (FFPE) blocks. Tissue sections of varying thickness, such as 5 μm, are cut from such tissue blocks and either left unmounted or mounted onto a solid support, such as a slide, by standard means. The cellular morphology of the tissue sample is revealed using a variety of fixatives and/or stains and visualized microscopically. If the density of cells, such as cancer cells, e.g., melanoma cells, in a tissue sample is sufficient (greater than about 1%), the section is scraped from the slide, and DNA can be extracted directly from the total tissue sample without further purification. Alternatively, if the density of cells, such as cancer cells, e.g., melanoma cells, in a tissue sample is low (less than about 1%), additional procedures to enrich the tissue sample for melanoma cells can be performed. DNA also can be isolated from fresh/frozen tissue, a fine-needle aspirate, or peripheral blood.

The sample may be prepared for assay using any suitable method as is known in the art. Desirably, the method extracts and concentrates nucleic acids. The method also desirably makes the target sequence accessible for amplification, and removes potential inhibitors of amplification from the extract.

DNA can be isolated from peripheral blood using, for example, a DNeasy DNA isolation kit, a QIAamp DNA blood kit, or a PAXgene blood DNA kit from Qiagen Inc. (Valencia, Calif.), or other methods known to one of ordinary skill in the art. DNA from other tissue samples also can be obtained using a DNeasy DNA isolation kit. Any other DNA extraction and purification technique also can be used, including liquid-liquid and solid-phase techniques ranging from phenol-chloroform extraction to automated magnetic bead nucleic acid capture systems. RNA can be isolated and reverse-transcribed and the resulting cDNA can be amplified (e.g., reverse-transcription polymerase chain reaction (RT-PCR) as described in U.S. Pat. Nos. 5,310,652; 5,322,770; 5,561,058; 5,641,864; and 5,693,517, for example).

Once nucleic acid has been obtained, it can be contacted with primers that result in specific amplification of a mutant sequence, if the mutant sequence is present in the sample. "Specific amplification" means that the primers amplify a specific mutant sequence and not other mutant sequences or the wild-type sequence. See, e.g., PCR Technology: Principles and Applications for DNA Amplification (Erlich, Editor, Freeman Press, NY (1992)); PCR Protocols: A Guide to Methods and Applications (Innis, et al., Editors, Academic Press, San Diego, Calif. (1990)); Current Protocols in Molecular Biology (Ausubel, 1994-1999, including supplemental updates through April 2004); and Molecular Cloning: A Laboratory Manual (Sambrook & Russell, 3rd ed., 2001). Allele-specific amplification-based methods or extension-based methods are described in Int'l Pat. App. Pub. No. WO 93/22456 and U.S. Pat. Nos. 4,851,331; 5,137,806; 5,595,890; and 5,639,611, all of which are specifically incorporated herein by reference for their teachings regarding same. While methods such as ligase chain reaction, strand displacement assay, and various transcription-based amplification methods can be used (see, e.g., review by Abramson and Myers, Current Opinion in Biotechnology 4:41-47 (1993)), PCR, in particular PCR employing clamps, such as PNA clamps, is preferred.

Multiple allele-specific primers, such as multiple mutant alleles or various combinations of wild-type and mutant alleles, can be employed simultaneously in a single amplification reaction. Amplification products can be distinguished by different labels or size (e.g., using gel electrophoresis).

A primer can be detectably labeled with a label that can be detected by spectroscopic, photochemical, biochemical, immunochemical or chemical means, for example (see, e.g., Sambrook, et al.). Useful labels include a dye, such as a fluorescent dye, a radioactive label, such as $^{32}P$, an electron-dense reagent, an enzyme, such as peroxidase or alkaline phosphatase, biotin, or haptens and proteins for which antisera or monoclonal antibodies are available.

A detectable oligonucleotide can be similarly labeled, such as with fluorescein. In this regard, if the primer is labeled with a dye and the detectable oligonucleotide is labeled with fluorescein and is designed to bind to the nascent strand opposite from the dye, fluorescence resonance energy transfer (FRET) across the DNA helix can occur. Other detectable oligonucleotides include a molecular probe, a TAQMAN® probe, a single-stranded DNA probe, a double-stranded DNA probe, and the like.

Any suitable sequence can be used as the IC. Examples of IC target sequences include those used in the EXAMPLES herein.

Nucleic acid amplification reagents include an enzyme having polymerase activity (e.g., AmpliTaq Gold®), one or more enzyme co-factors (e.g., $MgCl_2$), and deoxynucleotide triphosphates (dNTPs; e.g., dATP, dGTP, dCTP, and dTTP).

Conditions that promote amplification are those that promote annealing of primers and extension of nucleic acid sequences. Annealing is dependent on various parameters, such as temperature, ionic strength, length of sequences being amplified, complementarity, and G:C content of the sequences being amplified. For example, lowering the temperature promotes annealing of complementary nucleic acid sequences. High G:C content and longer length stabilize duplex formation. Generally, primers and detectable oligonucleotides of about 30 bp or less and having a high G:C content work well. Preferred amplification conditions, primers and detectable oligonucleotides are exemplified herein.

Amplification can be repeated any suitable number of times by thermal cycling the reaction mixture between about 10 and about 100 times, such as between about 20 and about 75 times, such as between about 25 and about 50 times.

Once the amplification reactions are completed, the presence of an amplified product can be detected using any suitable method. Such methods include, without limitation, those known in the art, such as gel electrophoresis with or without a fluorescent dye (depending on whether the product was amplified with a dye-labeled primer), a melting profile with an intercalating dye (see, e.g., PCR Technology, Principles, and Applications for DNA Amplification, Erlich, Ed., W.H. Freeman and Co., New York, 1992, Chapter 7), and hybridization with an internal detectable oligonucleotide. Other examples of methods include enzyme-linked immunosorbent assay (ELISA), electro-chemiluminescence, reverse dot blots, high pressure liquid chromatography (HPLC) (see, e.g., Lazar, Genome Res. 4: S1-S14 (1994)), and single-strand conformation polymorphism analysis of single-stranded PCR products also can be used (see, e.g., Orita, et al., PNAS USA 86: 2766-2770 (1989)).

Amplified nucleic acid can be detected by monitoring an increase in the total amount of double-stranded DNA (dsDNA) in the reaction mixture (see, e.g., U.S. Pat. No. 5,994,056 and European Pat. Pub. Nos. 487,218 and 512,334). A DNA-binding dye, such as SYBR Green, is used. The dye fluoresces when bound to dsDNA, and the increase in fluorescence is used to determine the increase in dsDNA.

Dideoxy sequencing-based methods and Pyrosequencing™ of oligonucleotide-length products also can be used to detect amplified nucleic acid. Another sequencing method is described by Kobayashi, et al., Mol. Cell. Detectable oligonucleotides 9: 175-182 (1995)).

When PCR is issued, conditions, such as those exemplified in the EXAMPLES herein, can be used. When standard PCR is used, detection can occur after amplification is complete, such as after using a labeled primer during amplification, by using a labeled primer as a detectable oligonucleotide after amplification, or by using a detectable oligonucleotide, which differs in sequence from the primers, after amplification to hybridize to the amplified target sequence. Labeled amplification products then can be separated and detected by other means.

Alternatively, the amplification and detection can be combined in a real-time PCR assay. When real-time PCR is used, the mixture can further comprise nucleic acid detection reagents, such as a non-specific fluorescent dye that intercalates with any double-stranded DNA, for example, or a sequence-specific DNA detectable oligonucleotide, which permits detection only after the detectable oligonucleotide hybridizes with its complementary DNA target, thereby enabling simultaneous amplification and detection. When a detectable oligonucleotide is present in the mixture during amplification, the detectable oligonucleotide should be stable under the conditions that promote amplification, should not interfere with amplification, should bind to its target sequence under amplification conditions, and emit a signal only upon binding its target sequence. Examples of detectable oligonucleotide that are particularly well-suited in this regard include molecular beacon detectable oligonucleotides, TAQMAN® detectable oligonucleotides, and linear detectable oligonucleotides, such as those described by Abravaya, et al. (U.S. Pat. App. Pub. No. 2005/0227257). The detectable oligonucleotides can form the loop region, alone or in further combination with part of the stem region, of a molecular beacon. The detectable oligonucleotides also can be used as linear detectable oligonucleotides with a fluorophore (e.g., FAM) at one end and a high-efficiency quencher, such as the Black Hole Quencher (BHQ®; Bio-Search Technologies, Inc., Novato, Calif.), at the other end.

The detection of an amplified product indicates, for example, that cells containing a specific mutant BRAF gene or genes (depending on whether or not two or more mutant BRAF genes are simultaneously detected) were present in the sample, while the lack of detection of an amplified product indicates that cells containing a specific mutant BRAF gene were not present in the sample, such as when cancer is present but has not metastasized. In this regard, if two or more specific mutant BRAF genes are amplified at the same time (or one or more specific mutant BRAF genes and wild-type BRAF), a primer for each specific mutant BRAF can be labeled with a distinct detectable label, thereby enabling the detection of two or more specific mutant BRAFs (or one or more specific mutant BRAFs and wild-type BRAF gene) to be distinguished. The relative levels of mutant and wild-type products can indicate the fraction of cells in the sample that contain a specific mutant BRAF gene. Lower fractions of cells containing the mutant BRAF sequence can indicate lower levels of metastasis, while higher fractions of cells containing the mutant sequence can indicate higher levels of metastasis.

If desired, the method can further comprise an initial universal amplification step. For example, the sample can be contacted with degenerate primers and amplified prior to specific amplification of one or more mutant BRAF genes, alone or in further combination with wild-type BRAF or an internal control sequence.

Preferably, the method employs a PNA clamp (see, e.g., Demers, et al., Nucleic Acids Res. 23: 3060-3065 (1995)). The PNA clamp preferably inhibits or prevents amplification of wild-type BRAF or whichever mutant BRAF gene is most prevalent in relation to the specific mutant BRAF gene to be amplified.

If desired, the nucleic acid sample or the detectable oligonucleotide can be immobilized on a solid support. Examples of assay formats utilizing solid supports include dot-blot formats and reverse dot-blot formats (see, e.g., U.S. Pat. Nos. 5,310,893; 5,451,512; 5,468,613; and 5,604,099, all of which are specifically incorporated herein by reference for their teachings regarding same).

Following amplification, it may be desirable to separate the amplification product from the template and the excess primer to determine whether specific amplification occurred. Separation can be effected by agarose, agarose-acrylamide or polyacrylamide gel electrophoresis using standard methodology (see, e.g., Sambrook, et al., Molecular Cloning, Fritsch and Maniatis, eds., Cold Spring Harbor Lab. Press, Cold Spring Harbor, N.Y. (1989)). Alternatively, chromatography can be used to effect separation. Examples of type of chromatography include adsorption, partition, ion-exchange and molecular sieve, and examples of types of chromatographic techniques include column, paper, thin-layer and gas chromatography (see, e.g., Freifelder, Physical Biochemistry Applications to Biochemistry and Molecular Biology, 2nd ed., Wm. Freeman & Co., New York, N.Y. (1982)).

Amplification is confirmed by visualization. For example, a gel stained with ethidium bromide can be visualized with UV light. Amplification products labeled with a radioisotope can be visualized by exposing and developing an x-ray film, whereas amplification products labeled with a fluorometric label can be visualized by subjecting the amplification products to stimulating spectra. A preferred method of visualization of amplification is the use of a labeled detectable oligonucleotide that hybridizes to the amplified products. A manual column, such as one available from Qiagen, also can be used.

The use of an automated sample preparation system, such as an automated sample preparation system designed to use magnetic microparticle processes for the purification of nucleic acids, can be preferred. An example of an automated sample preparation system is m2000sp, which is available from Abbott Laboratories, Abbott Park, Ill. Alternatively, samples can be prepared using the m24sp automated sample preparation system (Abbott) or prepared manually. Automated sample preparation is preferred over manual preparation because it is more consistent. Another example of a sample preparation kit is the QIAamp DNA FFPE tissue kit, which is available from Qiagen.

The Abbott mSample Preparation System$_{DNA}$ (4×24 preps; Abbott) reagents capture the nucleic acids and remove unbound sample components. Proteinase K is included in the lysis step to digest proteins associated with the samples. The bound nucleic acids are eluted and transferred to a 96-well deep plate. The nucleic acids are then ready for amplification. An unrelated DNA sequence, which serves as an internal control (IC) to demonstrate that the process has proceeded correctly for each sample, is introduced into the sample preparation procedure and is processed along with the calibrators, controls, and specimens.

Amplification/detection can be carried out as known in the art, such as by use of the m2000rt instrument (Abbott Molecular Inc., Des Plaines, Ill.). The target nucleic acid (e.g., DNA, RNA or both) is amplified by DNA polymerase reverse transcriptase in the presence of deoxynucleotide triphosphates (dNTPs) and an activation agent, for example, magnesium or manganese. The amplification reagent contains specific sets of amplification primers for the specific mutant (e.g., mutant BRAF) and, preferably, an IC. During PCR amplification, high temperature is used to separate the strands of double-stranded DNA. When the reaction is cooled to a temperature where DNA annealing can occur, the analyte-specific, single-stranded DNA oligonucleotide primers bind to the analyte DNA. The primers are extended by DNA polymerase, thereby making an exact copy of a short target stretch of the analyte DNA. The DNA polymerase can be, but need not be, a thermophilic enzyme that has been modified in its active site by a molecule that renders it inactive. When the enzyme is heated prior to the initiation of PCR, the inhibitory molecule is cleaved from the enzyme, thereby allowing it to regain its activity. In this manner, the enzyme is only active at temperatures where specific DNA-DNA interactions occur. This greatly reduces non-specific PCR artifacts, such as primer dimers. During each round of thermal cycling, amplification products dissociate to single strands at high temperature, allowing primer annealing and extension as the temperature is lowered. Exponential amplification of the target is achieved through repeated cycling between high and low temperatures. Amplification of the specific mutant (e.g., mutant BRAF) and, if present, the IC targets takes place simultaneously in the same reaction.

The method can be used to, for example, determine the BRAF mutation status for the purpose of evaluating treatment options with BRAF inhibitors, anti-EGFR monoclonal antibodies, MEK inhibitors, and the like. For example, Zelboraf™ (vemurafenib; Roche) reportedly has been shown to improve survival in people with BRAF V600E mutation-positive metastatic melanoma.

The method also can be used to predict outcome for a patient diagnosed with cancer, such as melanoma, to assess risk of metastasis, such as in patients with early stages of disease (stage I/II), such as melanoma, and to monitor patients with advanced, metastatic cancer, such as metastatic melanoma (stage III/IV). Since metastatic spread of cancer often occurs hematogenously, the method also can be used to assay peripheral blood to assess recurrence. Other cancers include, but are not limited to, thyroid (e.g., papillary thyroid carcinomas (PTC), ovary, colorectal, stomach, pancreas, Barrett's adenocarcinoma, pleural mesothelioma, non-Hodgkin's lymphoma, acute leukemia, squamous cell carcinoma of the head and neck, prostate, breast, ovary (e.g., low-grade serous carcinoma), hepatocellular carcinoma, sarcoma, pituitary, large intestine, biliary tract, eye, central nervous system, hematopoietic tissue, lymphoid tissue, rhabdomyosarcoma, sarcoma, glioma, cholangiocarcinoma, and lung adenocarcinoma.

In view of the above, a method of detecting at least one mutation (X) of a codon in a gene in a sample of DNA is also provided. The method comprises:

(a) performing an amplification reaction with the sample of DNA, wherein the amplification reaction comprises a primer, the last three nucleotides at the 3' terminus of which encodes X and wherein the fourth nucleotide from the 3' terminus contains a base other than adenine (A), wherein, if X is present, the primer anneals to X, whereupon, if X is present, the amplification reaction produces an amplification product comprising X, (b) detecting the amplification product comprising X, and wherein, if X is encoded by more than one codon, the amplification reaction comprises a primer for each codon. The amplification reaction can further comprise (iii) at least one peptide nucleic acid (PNA) clamp, wherein at least one PNA clamp blocks the amplification from wild-type target, and wherein, if the amplification reaction comprises one or more other PNA clamps, the PNA preferably clamps a detectable oligonucleotide and/or a primer. Detecting the amplification product comprising X can comprise detecting a labeled primer or contacting the amplification product with a detectable oligonucleotide and detecting hybridization of the detectable oligonucleotide to the amplification product comprising X. The amplification reaction can further comprise an internal control primer, in which case the amplification reaction also produces an amplification product comprising the internal control, in which case step (b) includes detecting the amplification product comprising the internal control. Detecting the amplification product comprising the internal control can comprise detecting a labeled primer or contacting the amplification product with a detectable oligonucleotide and detecting hybridization of the detectable oligonucleotide to the amplification product comprising the internal control. When the method comprises detecting two or more X, the method can comprise performing an amplification reaction with the sample of DNA for each X together or separately. In this regard, the method also can further comprise determining which X is present in the sample of DNA.

Primers, Detectable Oligonucleotides, and Method of Designing a Primer

A set of primers for amplification of V600X in exon 15 of the BRAF gene in a sample of nucleic acid from a human is also provided. The set of primers comprises primers, such as forward primers, each of which is an oligonucleotide, which is about 15 to about 35 nucleotides in length and comprises a nucleotide sequence encoding X at its 3' terminus. The set of primers comprising primers for amplification of V600E comprises one primer encoding GAA at its 3' terminus and another primer encoding GAG at its 3' terminus. The set of primers for amplification of V600K comprises one primer encoding AAA at its 3' terminus and another primer encoding AAG at its 3' terminus. The set of primers comprising primers for amplification of V600D comprises one primer encoding GAT at its 3' terminus and another primer encoding GAC at its 3' terminus. The set of primers for amplification of V600N comprises one primer encoding AAT at its 3' terminus and another primer comprising AAC at its 3' terminus. The set of primers comprising primers for amplification of V600R comprises a primer encoding CGT at its 3' terminus, a primer encoding CGC at its 3' terminus, a primer encoding CGA at its 3' terminus, a primer encoding CGG at its 3' terminus, a primer encoding AGA at its 3' terminus, and a primer encoding AGG at its 3' terminus. With regard to all of the aforementioned primers, the remainder of the nucleotide sequence (i.e., the nucleotide sequence up to the 3' terminal codon) should be such that a stable duplex will preferentially form between the primer and the exactly complementary allelic sequence encoding V600X. In other words, primers for amplification of V600E will preferentially amplify V600E but not others, such as V600, V600K, V600D, V600N, and V600R. Primers for amplification of V600K will preferentially amplify V600K but not V600E, V600D, V600N, and V600R. Primers for amplification of V600D will preferentially amplify V600D but not V600E, V600K, V600N, and V600R. Primers for amplification of V600N will preferentially amplify V600N but not V600E, V600K, V600D, and V600R. Preferably, a primer for amplification of V600E in which E is encoded by GAA will preferentially not amplify V600E in which E is encoded by GAG and vice versa, a primer for amplification of V600K in which K is encoded by AAA will preferentially not amplify V600K in which K is encoded by AAG and vice versa, a primer for amplification of V600D in which D is encoded by GAT will preferentially not amplify V600D in which D is encoded by GAC and vice versa, and a primer for amplification of V600N in which N is encoded by AAT will preferentially not amplify V600N in which N is encoded by AAC and vice versa. Likewise, a primer for amplification of V600R in which R is encoded by CGT will preferentially not amplify V600R in which R is encoded by CGC, CGA, CGG, AGA, and AGG, a primer for amplification of V600R in which R is encoded by CGC will preferentially not amplify V600R in which R is encoded by CGT, CGA, CGG, AGA, and AGG, a primer for amplification of V600R in which R is encoded by CGA will preferentially not amplify V600R in which R is encoded by CGT, CGC, CGG, AGA, and AGG, a primer for amplification of V600R in which R is encoded by CGG will preferentially not amplify V600R in which R is encoded by CGT, CGC, CGA, AGA, and AGG, a primer for amplification of V600R in which R is encoded by AGA will preferentially not amplify V600R in which R is encoded by CGT, CGC, CGA, CGG, and AGG, and a primer for amplification of V600R in which R is encoded by AGG will preferentially not amplify V600R in which R is encoded by CGT, CGC, CGA, CGG, and AGA. Preferably, the set of primers comprises at least one primer selected from the group consisting of:

(a) an oligonucleotide comprising the nucleotide sequence GGTCTAGCTACNGAA [SEQ ID NO: 59] at its 3' terminus and/or an oligonucleotide comprising the nucleotide sequence GGTCTAGCTACNGAG [SEQ ID NO: 60] at its 3' terminus, (b) an oligonucleotide comprising the nucleotide sequence GGTCTAGCTACNAAA [SEQ ID NO: 46] at its 3' terminus and/or an oligonucleotide comprising the nucleotide sequence GGTCTAGCTACNAAG [SEQ ID NO: 47] at its 3' terminus, (c) an oligonucleotide comprising the nucleotide sequence GGTCTAGCTACNGAT [SEQ ID NO: 48] at its 3' terminus and/or an oligonucleotide comprising the nucleotide sequence GGTCTAGCTACNGAC [SEQ ID NO: 49] at its 3' terminus, (d) an oligonucleotide comprising the nucleotide sequence GGTCTAGCTACNAAT [SEQ ID NO: 50] at its 3' terminus and/or an oligonucleotide comprising the nucleotide sequence GGTCTAGCTACNAAC [SEQ ID NO: 51] at its 3' terminus, (e) an oligonucleotide comprising the nucleotide sequence GGTCTAGCTACNCGT [SEQ ID NO: 52] at its 3' terminus, an oligonucleotide comprising the nucleotide sequence GGTCTAGCTACNCGC [SEQ ID NO: 53] at its 3' terminus, an oligonucleotide comprising the nucleotide sequence GGTCTAGCTACNCGA [SEQ ID NO: 54] at its 3' terminus, an oligonucleotide comprising the nucleotide sequence GGTCTAGCTACNCGG [SEQ ID NO: 55] at its 3' terminus, an oligonucleotide comprising the nucleotide sequence GGTCTAGCTACN AGA [SEQ ID NO: 56] at its 3' terminus, and an oligonucleotide comprising the nucleotide sequence GGTCTAGCTACNAGG [SEQ ID NO: 57] at its 3' terminus, (d) and (e),
(a) and (b),
(a) and (c),
(b) and (c),
(a), (b), and (c),
any of (a), (b), and (c), in further combination with (d),
any of (a), (b), and (c), in further combination with (e), and
any of (a), (b), and (c), in further combination with (d) and (e), wherein N is a nucleotide containing a base other than adenine (A), and wherein the oligonucleotide comprises from about 15 nucleotides to about 35 nucleotides. By "any of (a), (b), and (c)" is meant (a), (b), (c), (a) and (b), (a) and (c), (b) and (c), and (a), (b), and (c). The oligonucleotide can further comprise contiguous with the G at the 5' end of the nucleotide sequence one or more contiguous nucleotides of the nucleotide sequence 5' AATAGGTGATTTT 3' [SEQ ID NO: 58] starting with the T at the 3' end of the nucleotide sequence. The set of primers can further comprise a primer, such as a reverse primer, comprising from about 15 nucleotides to about 35 nucleotides, wherein, when the primer comprises 15-27 nucleotides, it comprises 15-27 contiguous nucleotides of SEQ ID NO: 10. The detectable oligonucleotide can comprise from about 15 nucleotides to about 35 nucleotides, wherein, when the detectable oligonucleotide comprises 15-20 nucleotides, it comprises 15-20 contiguous nucleotides of SEQ ID NO: 11.

Oligonucleotides can be prepared by any suitable method, usually chemical synthesis (e.g., solid-phase synthesis) employing commercially available reagents and instruments (see, e.g., Applied Biosystems, Inc. (Foster City, Calif.), DuPont (Wilmington, Del.), and Milligen (Bedford, Mass.)). Alternatively, they can be purchased through commercial sources. Methods of synthesizing oligonucleotides are well-known in the art (see, e.g., Narang, et al., Meth. Enzymol. 68: 90-99 (1979); Brown, et al., Meth. Enzymol. 68: 109-151 (1979); Beaucag, et al., Tetrahedron Lett. 22: 1859-1862 (1981); and U.S. Pat. No. 4,458,066).

Multiple allele-specific primers, based on the genetic codon for the identification of each mutated amino acid, are used. One primer is designed for each corresponding genetic codon encoding the mutation of interest at the 3' end plus an intended mutation at the fourth nucleotide from the 3' end. Allele-specific forward primers amplify variant specific targets based on select PCR amplification by a DNA polymerase, such as Taq polymerase, according to 3' matches between primers and template. A reverse transcriptase-DNA polymerase, such as rTth, also can be used in the context of the present methods. In this regard, a mixture of RNA polymerases, DNA polymerases, or RNA and DNA polymerases can be used. The reverse primer and detectable oligonucleotide are based on consensus sequences shared between reactions.

Thus, in view of the above, also provided is a method of designing a primer for detection of at least one mutation (X) of a codon in a gene in a sample of nucleic acid. The method comprises synthesizing a primer, the last three nucleotides at the 3' terminus of which encodes X and wherein the fourth nucleotide from the 3' terminus contains a base other than that which is present in the wild-type gene, whereupon a primer for detection of at least one mutation (X) in a codon in a gene in a sample of nucleic acid is designed. The method of designing primers based on the teachings of the present specification also include designing primers for the detection of more than one SNP and for detecting genes with target SNPs that also contain other, non-target mutants. Strategies for such primer design are given in Table 1.

Peptide nucleic acids (PNAs) are used as PCR clamping reagents that bind to complementary nucleic acid sequences with greater specificity and stability than their DNA counterparts (see, e.g., U.S. Pat. App. Pub. No. 2010/0009355 for discussion of PNA-based PCR clamping). The PNAs overlap with the forward primers and match perfectly the non-specific sequences to be blocked. As a result, the PNAs bind to the non-specific targets and inhibit the binding of primers to the same targets, thereby suppressing non-specific amplification (see FIG. 1).

Primers corresponding to a given amino acid position can be mixed for use in an assay to detect all possible variants of a specific mutation at that position. For example, allele-specific primers carrying GAG and GAA at their 3' end, respectively, can detect all possible variants for glutamic acid at amino acid position 600, such that all V600E mutations are detected (see, FIGS. 1 and 2).

The ability to carry out the method in a closed-tube, homogeneous format minimizes the risk of contamination (see, e.g., Kreuzer, et al., Ann. Hematol. 82: 284-289 (2003)). The sample can be contacted with a pair of primers by any means routinely applied for contacting a sample with a pair of PCR primers. For example, the sample and the primers can be contacted in a microwell plate or in a microvial adapted for the mixture of small volumes.

In view of the foregoing, provided are primers, such as forward primers, that amplify all possible V600E mutations in exon 15 of the human BRAF gene in a mutation-specific manner, primers, such as forward primers, that amplify all possible V600K mutations in exon 15 of the human BRAF gene in a mutation-specific manner, primers, such as forward primers, that amplify all possible V600D mutations in a mutation-specific manner, primers, such as forward primers, that amplify all possible V600R mutations in a mutation-specific manner, primers, such as forward primers, that amplify all possible V600N mutations in a mutation-specific manner, detectable oligonucleotides and PNAs to block the non-specific amplification of non-targeted BRAF sequences so as to increase specificity and sensitivity, and primers and detectable oligonucleotides to detect BRAF genomic sequences close to exon 15 to serve as internal controls (e.g., DNA adequacy, sample extraction, amplification efficiency, and standardization of the relative quantification of mutations (e.g., as a percentage of total wild-type and mutant alleles)). Also provided are diagnostic real-time PCR (rt-PCR) methods that use the aforementioned primers and detectable oligonucleotides to amplify and detect V600 mutations in exon 15 of the human BRAF gene in separate reactions or a pooled reaction.

Primers that are at least about 80% identical with the primers described herein also can be used. If desired, one or both primers (i.e., forward and reverse primers) can be tagged or labeled. Use of labeled primers results in labeled amplification products. Fluorescently labeled amplification products can be detected using any suitable equipment designed to detect fluorescence, such as the ABI 3100 Genetic Analyzer and Genescan 3.1.2 software (Applied Biosystems), for example.

While the methods described herein are based on the detection of genomic, DNA, RNA-based assays can be used. However, such assays are based on reverse transcription and subsequent amplification of mRNA from whole blood. While the sensitivity of mRNA-based methods generally is good, RNA degradation and low efficiency of the reverse transcriptase can limit, even severely limit, the practicality of such assays. In addition, because the amount of mRNA of interest can vary widely, for example, depending on the metabolic state of the circulating cells, the results of the assays can be difficult to reproduce.

If desired, the primers described above can be modified so that they no longer act as primers for DNA synthesis and can be labeled and used as detectable oligonucleotides. The detectable oligonucleotides can be used in different assay formats to detect a mutation (X) of the codon encoding valine at amino acid position 600 (V600X) in exon 15 of the BRAF gene in a sample of nucleic acid, such as DNA. For example, the detectable oligonucleotides can be used in a 5'-nuclease assay (see, e.g., U.S. Pat. Nos. 5,210,015; 5,487,972; and 5,804,375; and Holland, et al., PNAS USA 88:

7276-7280 (1988), all of which are specifically incorporated by reference for their teachings regarding same).

While the primers and detectable oligonucleotides have been described herein in the context of their use in nucleic acid-based amplification methods, such as PCR, in particular real-time PCR, such primers and detectable oligonucleotides can be useful as detectable oligonucleotides in other nucleic acid-based methods, such as hybridization techniques (e.g., membrane-based hybridization techniques (Southern blots and Northern blots), modified nucleic acid hybridization techniques (see, e.g., Pandian, et al., U.S. Pat. No. 5,627,030), and enzyme-linked immunoadsorbent assay (ELISA)-like techniques), which are used to detect identical, similar and complementary polynucleotide sequences.

The detectable oligonucleotides, which are single-stranded, linear DNA oligonucleotides, are detectably labeled in accordance with methods known in the art. Alternatively, primers can be similarly labeled, if desired. Any suitable label, such as a fluorophore, a luminophore, a chemiluminophore, a photoluminophore, or a radioisotope, can be used. For example, a fluorescent moiety can be covalently linked to one end of the detectable oligonucleotide and a quenching moiety can be covalently linked to the other end. Examples of suitable fluorophores include, but are not limited to, FAM (e.g., 6'-FAM), fluorescein and derivatives thereof, rhodamine, coumarin and derivatives thereof, TET, HEX, JOE, TAMA, TAMRA, NTB, ROX, VIC, NED, 4,7-dichloro-fluorescein, 4,7-dichloro-rhodamine, DABCYL, DABSYL, malachite green, LC-Red 610, LC-Red 640, LC-Red 670, LC-Red 705, Lucifer yellow, TEXAS RED®, tetramethylrhodamine, tetrachloro-6-carboxyfluoroscein, 5-carboxyrhodamine, and cyanine dyes (e.g., Cy3 and Cy5) and derivatives thereof. FAM is a preferred label. Examples of quenchers include DABCYL, DABSYL, DABMI, tetramethylrhodamine, TAMRA, and BHQ® dyes. As indicated above, during each round of real-time PCR amplification, the detectably labeled detectable oligonucleotides anneal to the amplified target DNA, if present. In the absence of a target sequence, each of the detectable oligonucleotides adopts a conformation that brings the quencher close enough to the excited fluorophore to absorb its energy before it can be fluorescently emitted. In the presence of a target sequence, each detectable oligonucleotide binds to its complementary sequence in the target and the fluorophore and the quencher are held apart, allowing fluorescent emission and detection. Preferably, the target-specific detectable oligonucleotides and the IC-specific detectable oligonucleotides are labeled differently so that target DNA and IC DNA can be distinguished. In this regard, the target-specific detectable oligonucleotide(s) is/are preferably labeled with FAM and quenched with BHQ-1.

Kit

A kit is also provided. The kit comprises:

(i) a set of primers for detection of V600X in exon 15 of the BRAF gene in a sample of nucleic acid from a human, wherein the set of primers comprises at least one primer selected from the group consisting of:

(a) an oligonucleotide comprising the nucleotide sequence GGTCTAGCTACNGAA [SEQ ID NO: 59] at its 3' terminus and/or an oligonucleotide comprising the nucleotide sequence GGTCTAGCTACNGAG [SEQ ID NO: 60] at its 3' terminus, (b) an oligonucleotide comprising the nucleotide sequence GGTCTAGCTACNAAA [SEQ ID NO: 46] at its 3' terminus and/or an oligonucleotide comprising the nucleotide sequence GGTCTAGCTACNAAG [SEQ ID NO: 47] at its 3' terminus, (c) an oligonucleotide comprising the nucleotide sequence GGTCTAGCTACNGAT [SEQ ID NO: 48] at its 3' terminus and/or an oligonucleotide comprising the nucleotide sequence GGTCTAGCTACNGAC [SEQ ID NO: 49] at its 3' terminus, (d) an oligonucleotide comprising the nucleotide sequence GGTCTAGCTACNAAT [SEQ ID NO: 50] at its 3' terminus and/or an oligonucleotide comprising the nucleotide sequence GGTCTAGCTACNAAC [SEQ ID NO: 51] at its 3' terminus, (e) an oligonucleotide comprising the nucleotide sequence GGTCTAGCTACNCGT [SEQ ID NO: 52] at its 3' terminus, an oligonucleotide comprising the nucleotide sequence GGTCTAGCTACNCGC [SEQ ID NO: 53] at its 3' terminus, an oligonucleotide comprising the nucleotide sequence GGTCTAGCTACNCGA [SEQ ID NO: 54] at its 3' terminus, an oligonucleotide comprising the nucleotide sequence GGTCTAGCTACNCGG [SEQ ID NO: 55] at its 3' terminus, an oligonucleotide comprising the nucleotide sequence GGTCTAGCTACN AGA [SEQ ID NO: 56] at its 3' terminus, and an oligonucleotide comprising the nucleotide sequence GGTCTAGCTACNAGG [SEQ ID NO: 57] at its 3' terminus, (d) and (e),
(a) and (b),
(a) and (c),
(b) and (c),
(a), (b), and (c),
any of (a), (b), and (c), in further combination with (d),
any of (a), (b), and (c), in further combination with (e), and
any of (a), (b), and (c), in further combination with (d) and (e), wherein N is a nucleotide containing a base other than adenine (A), and wherein the oligonucleotide comprises from about 15 nucleotides to about 35 nucleotides, and (ii) instructions for a method of detecting a mutation (X) of the codon encoding valine at amino acid position 600 (V600X) in exon 15 of the BRAF gene in a sample of nucleic acid from a human, which method comprises:

(a) performing an amplification reaction with the sample of nucleic acid, wherein the amplification reaction comprises a primer, the last three nucleotides at the 3' terminus of which encodes X and wherein the fourth nucleotide from the 3' terminus contains a base other than adenine (A), wherein, if X is present, the primer anneals to X, and at least one peptide nucleic acid (PNA) clamp, wherein at least one PNA clamp blocks the amplification from wild-type target, wherein, if the sample of nucleic acid is mRNA, step (a) further comprises obtaining cDNA reverse-transcribed from the mRNA or reverse-transcribing cDNA from the mRNA before performing the amplification reaction, whereupon, if X is present, the amplification reaction produces an amplification product comprising X, and (b) detecting the amplification product comprising X, wherein, if X is encoded by more than one codon, the amplification reaction comprises a primer for each codon, wherein, if the method comprises detecting two or more X, the method can comprise performing an amplification reaction with the sample of nucleic acid for each X together or separately, and wherein the method also can further comprise determining which X is present in the sample of nucleic acid. The oligonucleotide can further comprise contiguous with the G at the 5' end of the nucleotide sequence one or more contiguous nucleotides of the nucleotide sequence 5' AATAGGTGATTTT 3' [SEQ ID NO: 58] starting with the T at the 3' end of the nucleotide sequence. The kit can further comprise a primer, such as a reverse primer, comprising from about 15 nucleotides to about 35 nucleotides, wherein, when the primer comprises 15-27 nucleotides, it comprises 15-27 contiguous nucleotides of SEQ ID NO: 10.

The kit can further comprise a detectable oligonucleotide comprising from about 15 nucleotides to about 35 nucleotides, wherein, when the detectable oligonucleotide comprises 15-20 nucleotides, it comprises 15-20 contiguous nucleotides of SEQ ID NO: 11. X can be at least one amino acid selected from the group consisting of E, K, D, R, and N. X can be at least one amino acid selected from the group consisting of E, K, and D, such as E, E and K, E and D, K and D, or E, K, and D. An example of a label is FAM. In this regard, the label FAM is preferably used in combination with the quencher BHQ-1.

A kit can contain a container or a sample vial for storing a sample of a tissue or a body fluid. The primers, such as a pair of primers, specifically a forward primer and a reverse primer, can be in a composition in amounts effective to permit detection of mutant sequences. Detection of mutant sequences is accomplished using any of the methods described herein or known in the art for detecting a specific nucleic acid molecule in a sample, A kit can also comprise buffers, nucleotide bases, and other compositions to be used in hybridization and/or amplification reactions.

The kit can further comprise dNTPs. Preferably, the dNTPs are supplied in a buffered solution with a reference dye.

The primers, detectable oligonucleotides and dNTPs can be packaged in various configurations. Preferably, the primers, detectable oligonucleotides and dNTPS are in a single container. The container preferably also contains a preservative, such as sodium azide and/or ProClin® 950.

The kit can further comprise a DNA polymerase, an RNA polymerase, a reverse transcriptase, and a mixture of two or more of the foregoing. Any suitable DNA polymerase can be used. An example of a preferred DNA polymerase is Ampli-Taq Gold® (Life Technologies Corp., Carlsbad, Calif.). Likewise, any suitable RNA polymerase can be used. An example of a preferred reverse transcriptase-DNA polymerase is rTth. The polymerase can be supplied in a buffered solution, which optionally contains, and preferably does not contain, stabilizers.

The kit can further comprise an activation reagent, such as magnesium chloride, in a buffered solution. The buffered solution preferably includes a preservative, such as sodium azide and/or ProClin® 950.

The kit can optionally further comprise an IC. The IC is an unrelated DNA sequence that demonstrates that the process has proceeded correctly for each sample. Any suitable sequence can be used as the IC. Examples of IC target sequences include those set forth in the EXAMPLES herein. The target-specific detectable oligonucleotides and the IC-specific detectable oligonucleotides are labeled differently so that target DNA and IC DNA can be distinguished. An example of a label for the IC-specific detectable oligonucleotide is Cy5. Preferably, the label Cy5 is used in combination with the quencher BHQ-2.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation (s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

EXAMPLES

The following examples serve to illustrate the present disclosure. The examples are not intended to limit the scope of the claimed invention in any way.

Example 1

This example describes reactions for detection of individual SNPs at V600 in exon 15 of the BRAF gene in DNA.

Two alleles (i.e., codons) are possible for V600E, V600K, and V600D mutation (i.e., GAG and GAA for glutamic acid (E), AAG and AAA for lysine (K), and GAT and GAC for aspartic acid (D)). Each forward primer was designed to amplify preferentially a specific codon. Thus, two forward primers are included in each reaction to ensure the complete detection of each amino acid mutation.

BRAF reverse primer and, when used, detectable oligonucleotide target consensus sequences. Therefore, the reverse primer and, when used, the detectable oligonucleotide can be the same for all reactions.

Internal control primers and detectable oligonucleotide target a sequence within exon 13 of the BRAF gene. They were the same for all reactions.

PNAs, which are very short, non-extendable oligonucleotides, are included to block potential non-specific amplification. They bind to their complementary target sequences in a highly sequence-specific manner. Since PNA sequences are on the same strand as the forward primer, they compete with the forward primer and prevent non-specific amplification. Even though there are multiple non-specific SNPs for any given mutation-specific PCR, only the most prevalent ones, which may generate non-specific amplification, need to be blocked by PNAs, such as wild-type and V600K in the case of V600E detection, wild-type and V600E in the case of V600K detection, and wild-type in the case of V600D detection.

The method comprised forming a mixture containing the oligonucleotides and other components essential for nucleic acid amplification (e.g., dNTP mix, buffer, enzyme, and divalent ion as activation agent), combining the mixture with purified nucleic acids, and subjecting the reaction mixture to specific conditions to amplify and detect the target sequences. The processes were carried out in a closed tube format by an instrument capable of concurrent thermal cycling and signal detection. Genomic DNA extracted from cell lines, formalin-fixed paraffin-embedded (FFPE) cell lines, and clinical FFPE tumor samples was assayed. The specificity of the assay was evaluated using genomic DNA extracted from cell lines that carry wild-type or various BRAF mutations. The sensitivity was evaluated using a mixture of wild-type BRAF cells and V600E mutant BRAF cells at defined ratios.

TABLE 1

V600E Reaction

| Oligonucleotide | Sequence and Label (5'→3' for DNA and N→C for PNA) | Concentration** |
| --- | --- | --- |
| BRAF V600E forward primer 1 | AATAGGTGATTTTGGTCTAGCTACCGAG [SEQ ID NO: 8] | 0.2 µM |
| BRAF V600E forward primer 2 | AATAGGTGATTTTGGTCTAGCTACCGAA [SEQ ID NO: 9] | 0.2 µM |
| BRAF reverse primer | TAATCAGTGGAAAAATAGCCTCAATTC [SEQ ID NO: 10] | 0.2 µM |
| BRAF detectable oligonucleotide | FAM-LGGAGLGGGLFFFALFAGLL-BHQ1-dT* [SEQ ID NO: 11] | 0.2 µM |
| BRAF wild-type PNA | GCTACAGTGAAATCTCG [SEQ ID NO: 12] | 1 µM |
| BRAF V600 K PNA | GCTACAAAGAAATCTCG [SEQ ID NO: 13] | 1 µM |
| Internal Control exon 13 forward primer | GTATCACCATCTCCATATCATTGAGACC [SEQ ID NO: 14] | 0.2 µM |
| Internal Control exon 13 reverse primer | ACAAGACATTTAACGAATGGAACTTACTC [SEQ ID NO: 15] | 0.2 µM |
| Internal Control exon 13 detectable oligonucleotide | Quasar-GFAFGAFAGAFLGFAFAGG-BHQ2-dT* [SEQ ID NO: 16] | 0.2 µM |
| PCR oligo buffer | | 0.632 X |
| dNTPs | | 0.4 mM |
| ROX | | 0.0147 µM |
| TaqGold | | 11 Units |
| MgCl₂ | | 4 mM |

*F = 5-Propynyl dC, L = 5-Propynyl dU
**Concentration in 50 µl reaction consisting of 25 µl target and 25 µl PCR reagents

TABLE 2

V600K Reaction

| Oligonucleotide | Sequence and Label (5'→3' for DNA and N→C for PNA) | Concentration** |
| --- | --- | --- |
| BRAF V600K forward primer 1 | AATAGGTGATTTTGGTCTAGCTACTAAG [SEQ ID NO: 17] | 0.2 µM |
| BRAF V600K forward primer 2 | AATAGGTGATTTTGGTCTAGCTACTAAA [SEQ ID NO: 18] | 0.2 µM |
| BRAF reverse primer | TAATCAGTGGAAAAATAGCCTCAATTC [SEQ ID NO: 10] | 0.2 µM |
| BRAF detectable oligonucleotide | FAM-LGGAGLGGGLFFFALFAGLL-BHQ1-dT* [SEQ ID NO: 11] | 0.2 µM |

TABLE 2-continued

V600K Reaction

| Oligonucleotide | Sequence and Label (5'→3' for DNA and N→C for PNA) | Concentration** |
| --- | --- | --- |
| BRAF wild-type PNA | GCTACAGTGAAATCTCG [SEQ ID NO: 12] | 1 µM |
| BRAF V600E PNA | GCTACAGAGAAATCTCG [SEQ ID NO: 19] | 1 µM |
| Internal Control exon 13 forward primer | GTATCACCATCTCCATATCATTGAGACC [SEQ ID NO: 14] | 0.2 µM |
| Internal Control exon 13 reverse primer | ACAAGACATTTAACGAATGGAACTTACTC [SEQ ID NO: 15] | 0.2 µM |
| Internal Control exon 13 detectable oligonucleotide | Quasar-GFAFGAFAGAFLGFAFAGG-BHQ2-dT* [SEQ ID NO: 16] | 0.2 µM |
| PCR oligo buffer | | 0.632 X |
| dNTPs | | 0.4 mM |
| ROX | | 0.0147 µM |
| TaqGold | | 11 Units |
| MgCl$_2$ | | 4 mM |

*F = 5-Propynyl dC, L = 5-Propynyl dU
**Concentration in reaction of 25 µl target and 25 µl PCR reagents

TABLE 3

V600D Reaction

| Oligonucleotide | Sequence and Label (5'→3' for DNA and N→C for PNA) | Concentration** |
| --- | --- | --- |
| BRAF V600D forward primer 1 | AATAGGTGATTTTGGTCTAGCTACTGAT [SEQ ID NO: 20] | 0.2 µM |
| BRAF V600D forward primer 2 | AATAGGTGATTTTGGTCTAGCTACTGAC [SEQ ID NO: 21] | 0.2 µM |
| BRAF reverse primer | TAATCAGTGGAAAAATAGCCTCAATTC [SEQ ID NO: 10] | 0.2 µM |
| BRAF detectable oligonucleotide | FAM-LGGAGLGGGLFFFALFAGLL-BHQ1-dT* [SEQ ID NO: 11] | 0.2 µM |
| BRAF wild-type PNA | GCTACAGTGAAATCTCG [SEQ ID NO: 12] | 1 µM |
| Internal Control exon 13 forward primer | GTATCACCATCTCCATATCATTGAGACC [SEQ ID NO: 14] | 0.2 µM |
| Internal Control exon 13 reverse primer | ACAAGACATTTAACGAATGGAACTTACTC [SEQ ID NO: 15] | 0.2 µM |
| Internal Control exon 13 detectable oligonucleotide | Quasar- GFAFGAFAGAFLGFAFAGG -BHQ2-dT* [SEQ ID NO: 16] | 0.2 µM |
| PCR oligo buffer | | 0.632 X |
| dNTPs | | 0.4 mM |
| ROX | | 0.0147 µM |
| TaqGold | | 11 Units |
| MgCl$_2$ | | 4 mM |

*F = 5-Propynyl dC, L = 5-Plopynyl dU
**Concentration in reaction of 25 µl target and 25 µl PCR reagents PCR cycling included one cycle at 92° C. for 10 minutes (TaqGold activation) and 55 cycles (the number of cycles can be modified) of 88° C./5 seconds, 92° C./15 seconds, 67° C./5 seconds, and 63° C./35 seconds (DNA amplification and fluorescence readings). Alternatively, PCR cycling can include one cycle at 92° C. for 10 minutes (TaqGold activation) and 55 cycles of 92° C. for 15 seconds, and 65° C. for 35 seconds (DNA amplification and fluorescence readings).

A linearity study on 10 ng genomic DNA using the V600E assay and the V600K assay revealed a good linear relationship. A linearity study on 2.5 ng genomic DNA extracted from FFPE cell line samples using the V600E assay also revealed a good linear relationship.

Other mutations can be detected in the same manner. Allele-specific primers can be designed for other mutations in the same manner as described above for V600E/K/D SNPs.

Example 2

This example describes a pooled reaction for detection of multiple SNPs at V600 in exon 15 of the BRAF gene.

Two or more of BRAF V600E, V600K, and V600D mutations also can be detected in a pooled reaction.

TABLE 4

V600 E/K/D Pooled Reaction

| Oligonucleotide | Sequence and Label (5'→3' for DNA and N→C for PNA) | Concentration** |
| --- | --- | --- |
| BRAF V600E forward primer 1 | AATAGGTGATTTTGGTCTAGCTACCGAG [SEQ ID NO: 8] | 0.2 µM |
| BRAF V600E forward primer 2 | AATAGGTGATTTTGGTCTAGCTACCGAA [SEQ ID NO: 9] | 0.2 µM |
| BRAF V600K forward primer 1 | AATAGGTGATTTTGGTCTAGCTACTAAG [SEQ ID NO: 17] | 0.2 µM |
| BRAF V600K forward primer 2 | AATAGGTGATTTTGGTCTAGCTACTAAA [SEQ ID NO: 18] | 0.2 µM |
| BRAF V600D forward primer 1 | AATAGGTGATTTTGGTCTAGCTACTGAT [SEQ ID NO: 20] | 0.2 µM |
| BRAF V600D forward primer 2 | AATAGGTGATTTTGGTCTAGCTACTGAC [SEQ ID NO: 21] | 0.2 µM |
| BRAF reverse primer | TAATCAGTGGAAAAATAGCCTCAATTC [SEQ ID NO: 10] | 0.2 µM |
| BRAF detectable oligonucleotide | FAM- LGGAGLGGGLFFFALFAGLL -BHQ1-dT* [SEQ ID NO: 11] | 0.2 µM |
| BRAF wild-type PNA | GCTACAGTGAAATCTCG [SEQ ID NO: 12] | 0.2 µM |
| Internal Control exon 13 forward primer | GTATCACCATCTCCATATCATTGAGACC [SEQ ID NO: 14] | 0.2 µM |
| Internal Control exon 13 reverse primer | ACAAGACATTTAACGAATGGAACTTACTC [SEQ ID NO: 15] | 0.2 µM |
| Internal Control exon 13 detectable oligonucleotide | Quasar- GFAFGAFAGAFLGFAFAGG -BHQ2-dT* [SEQ ID NO: 16] | 0.2 µM |
| BRAF wild-type PNA | GCTACAGTGAAATCTCG [SEQ ID NO: 12] | 1 µM |
| PCR oligo buffer | | 0.632 X |
| dNTPs | | 0.4 mM |
| ROX | | 0.0147 µM |
| TaqGold | | 11 Units |
| MgCl$_2$ | | 4 mM |

*F = 5-Propynyl dC, L = 5-Propynyl dU
**Concentration in reaction of 25 µl target and 25 µl PCR reagents PCR cycling included one cycle at 92° C. for 10 minutes (TaqGold activation) and 55 cycles (the number of cycles can be modified without impacting assay performance) of 88° C./5 seconds, 92° C./15 seconds, 67° C./5 seconds, and 63° C./35 seconds (DNA amplification and fluorescence readings). Alternatively, PCR cycling can include one cycle at 92° C. for 10 minutes (TaqGold activation) and 55 cycles of 92° C. for 15 seconds, and 65° C. for 35 seconds (DNA amplification and fluorescence readings).

Other mutations can be detected in the same manner. Allele-specific primers can be designed for other mutations in the same manner as described above for V600E/K/D SNPs. In this regard, the pooled reaction can detect one or more of V600E, V600K and/or V600D in combination with one or more other mutations.

Example 3

This example describes alternative forward primers and detectable oligonucleotides for use in the methods.

TABLE 5

Alternative Primers and Detectable oligonucleotides

| Oligonucleotide | Sequence and Label (5'→3' and N→C for PNA) | Mutation detected at V600 of BRAF |
|---|---|---|
| BRAF Forward primer FPd MU2 | AATAGGTGATTTTGGTCTAGCTACAAA [SEQ ID NO: 22] | E, K, D, R, N |
| BRAF Forward primer Fpd MU3 | AATAGGTGATTTTGGTCTAGCTACCGA [SEQ ID NO: 23] | E, D |
| BRAF Forward primer FPd MU4 | AATAGGTGATTTTGGTCTAGCTACGGA [SEQ ID NO: 24] | E, D |
| BRAF Forward primer MU-f1a | AATAGGTGATTTTGGTCTAGCTACTGAG [SEQ ID NO: 25] | E |
| BRAF Forward primer MU-f1c | AATAGGTGATTTTGGTCTAGCTACGGAG [SEQ ID NO: 26] | E |
| BRAF Forward primer MU-f2a | AATAGGTGATTTTGGTCTAGCTACTGAA [SEQ ID NO: 27] | E |
| BRAF Forward primer MU-f2c | AATAGGTGATTTTGGTCTAGCTACGGAA [SEQ ID NO: 28] | E |
| BRAF Forward primer MU-f3b | AATAGGTGATTTTGGTCTAGCTACCAAG [SEQ ID NO: 29] | K |
| BRAF Forward primer MU-f3c | AATAGGTGATTTTGGTCTAGCTACGAAG [SEQ ID NO: 30] | K |
| BRAF Forward primer MU-f4b | AATAGGTGATTTTGGTCTAGCTACCAAA [SEQ ID NO: 31] | K |
| BRAF Forward primer MU-f4c | AATAGGTGATTTTGGTCTAGCTACGAAA [SEQ ID NO: 32] | K |
| BRAF Forward primer FPd MU9 | AATAGGTGATTTTGGTCTAGCTACAAAC [SEQ ID NO: 33] | K, N |
| BRAF Forward primer FPd MU10 | AATAGGTGATTTTGGTCTAGCTACAAAT [SEQ ID NO: 34] | K, D, N |
| BRAF Forward primer FPd MU11 | AATAGGTGATTTTGGTCTAGCTACAAC [SEQ ID NO: 35] | K, R, N |
| BRAF Forward primer FPd MU12 | AATAGGTGATTTTGGTCTAGCTACGAA [SEQ ID NO: 36] | K, N |
| BRAF Forward primer FPd MU13 | AATAGGTGATTTTGGTCTAGCTACCAA [SEQ ID NO: 37] | K, N |
| Internal Control exon 17 forward primer | GATCTCAGTAAGGTACGGAGTAACTGTC [SEQ ID NO: 38] | |
| Internal Control exon 17 reverse primer | TAGTCTGTTCTTTTGGATAGCATGAAGCT [SEQ ID NO: 39] | |
| Internal Control exon 17 detectable oligonucleotide | Quasar-GALGAGAGAFFAFLFLLLFF-BHQ2-dT* [SEQ ID NO: 40] | |

TABLE 5-continued

Alternative Primers and Detectable oligonucleotides

| Oligonucleotide | Sequence and Label (5'→3' and N→C for PNA) | Mutation detected at V600 of BRAF |
|---|---|---|
| Internal Control exon 14 forward primer | CTAAATAAGTCTTTACACCCCCAAGTATGTTC [SEQ ID NO: 41] | |
| Internal Control exon 14 reverse primer | CTGTGGATGATTGACTTGGCGTGTAAG [SEQ ID NO: 42] | |
| Internal Control exon 14 detectable oligonucleotide | Quasar-AGALLLFGAGGFFAGAGLFF-BHQ2-dT* [SEQ ID NO: 43] | |

*F = 5-Propynyl dC, L = 5-Propynyl dU

Example 4

This example describes reactions for detection of individual SNPs at V600 in exon 15 of the BRAF gene in mRNA.

Total nucleic acids or RNA from human FFPE tumor tissues are used as a template for the reverse transcription/PCR amplification reaction. Total nucleic acids are isolated and purified from FFPE samples using a purification kit such as QIAmp FFPE DNA tissue kit (Qiagen) without RNase treatment. RNA can be isolated and purified from FFPE samples using an RNA purification kit such as RNeasy kit (Qiagen), sometimes together with DNase treatment. For RNA detection, reverse transcription is initiated from a reverse primer (BRAF-R3) that anneals to a sequence within exon 15 of the BRAF gene. This BRAF sequence element is common to all BRAF exon 15 containing transcripts; therefore, the single reverse primer can promote reverse transcription of all targeted variants from RNA. PCR amplification of the resulting cDNA is directed by the above-mentioned reverse primer in combination with multiple forward primers that specifically anneal to BRAF V600E, V600K, or V600D sequences at the SNP sites. The same primers can also be used to amplify genomic DNA containing targeted variants.

In addition to the primer/detectable oligonucleotide set that detects V600E, V600K, or V600D from total nucleic acid or RNA, a primer/detectable oligonucleotide set is designed to detect a sequence within BRAF exon 13 as internal control. The amplification levels of BRAF exon 13 are used to normalize the BRAF variants detection process against variations in sample adequacy, sample extraction process, total BRAF RNA expression level and amplification efficiency. In order to amplify both RNA and genomic DNA, BRAF internal control primer 2 is designed within exon 13.

The reaction formulation and cycling condition for detection from RNA and/or total nucleic acids can be same or similar to those of the V600E, V600K, or V600D reaction in the DNA SNP assay (see, e.g., Example 1), with the exceptions that the cycling condition contains a reverse transcription step prior to the normal thermal cycling program and may contain a different enzyme. PCR reaction is set up containing the oligonucleotides as shown in Tables 6, 7, and 8.

It is sometimes desired that only RNA, not genomic DNA, is detected for BRAF V600 mutations and the internal control. To achieve that, in addition to the RNA-specific sample preparation, the reverse primer can be designed to be located at the adjacent exon, i.e., exon 16 for V600 mutations and exon 14 for the internal control, such as within the exon or straddling an exon-exon junction. Due to the long intron sequences between exons 15 and 16 and between exons 13 and 14, such PCR oligo designs can only amplify RNA (without introns), and not genomic DNA (with introns), for both BRAF V600 mutations and internal control.

TABLE 6

| V600E Reaction | |
|---|---|
| Oligonucleotide | Sequence and label (5'→3' for DNA and N→C for PNA) |
| BRAF V600E forward primer 1 | AATAGGTGATTTTGGTCTAGCTACCGAG [SEQ ID NO: 8] |
| BRAF V600E forward primer 2 | AATAGGTGATTTTGGTCTAGCTACCGAA [SEQ ID NO: 9] |
| BRAF reverse primer 2 | CACAAAATGGATCCAGACAACTGTTC [SEQ ID NO: 44] |
| BRAF detectable oligonucleotide | FAM-LGGAGLGGGLFFFALFAGLL-BHQ1-dT* [SEQ ID NO: 11] |
| BRAF wild-type PNA | GCTACAGTGAAATCTCG [SEQ ID NO: 12] |
| BRAF V600K PNA | GCTACAAAGAAATCTCG [SEQ ID NO: 13] |

TABLE 6-continued

V600E Reaction

| Oligonucleotide | Sequence and label (5'→3' for DNA and N→C for PNA) |
|---|---|
| Internal Control forward primer | GTATCACCATCTCCATATCATTGAGACC [SEQ ID NO: 14] |
| Internal Control reverse primer | TCCATGCCCTGTGCAGTCTGTCGTG [SEQ ID NO: 45] |
| Internal Control detectable oligonucleotide | Quasar-GFAFGAFAGAFLGFAFAGG-BHQ2-dT* [SEQ ID NO: 16] |

*F = 5-Propynyl dC, L = 5-Propynyl dU

TABLE 7

V600K Reaction

| Oligonucleotide | Sequence and label (5'→3' for DNA and N→C for PNA) |
|---|---|
| BRAF V600K forward primer 1 | AATAGGTGATTTTGGTCTAGCTACTAAG [SEQ ID NO: 17] |
| BRAF V600K forward primer 2 | AATAGGTGATTTTGGTCTAGCTACTAAA [SEQ ID NO: 18] |
| BRAF reverse primer 2 | CACAAAATGGATCCAGACAACTGTTC [SEQ ID NO: 44] |
| BRAF detectable oligonucleotide | FAM-LGGAGLGGGLFFFALFAGLL-BHQ1-dT* [SEQ ID NO: 11] |
| BRAF wild-type PNA | GCTACAGTGAAATCTCG [SEQ ID NO: 12] |
| BRAF V600E PNA | GCTACAGAGAAATCTCG [SEQ ID NO: 19] |
| Internal Control forward primer | GTATCACCATCTCCATATCATTGAGACC [SEQ ID NO: 14] |
| Internal Control reverse primer 2 | TCCATGCCCTGTGCAGTCTGTCGTG [SEQ ID NO: 45] |
| Internal Control detectable oligonucleotide | Quasar-GFAFGAFAGAFLGFAFAGG-BHQ2-dT* [SEQ ID NO: 16] |

*F = 5-Propynyl dC, L = 5-Propynyl dU

TABLE 8

V600D Reaction

| Oligonucleotide | Sequence and label (5'→3' for DNA and N→C for PNA) |
|---|---|
| BRAF V600D forward primer 1 | AATAGGTGATTTTGGTCTAGCTACTGAT [SEQ ID NO: 20] |
| BRAF V600D forward primer 2 | AATAGGTGATTTTGGTCTAGCTACTGAC [SEQ ID NO: 21] |
| BRAF reverse primer 2 | CACAAAATGGATCCAGACAACTGTTC [SEQ ID NO: 44] |
| BRAF detectable oligonucleotide | FAM-LGGAGLGGGLFFFALFAGLL-BHQ1-dT* [SEQ ID NO: 11] |
| BRAF wild-type PNA | GCTACAGTGAAATCTCG [SEQ ID NO: 12] |
| Internal Control forward primer | GTATCACCATCTCCATATCATTGAGACC [SEQ ID NO: 14] |
| Internal Control reverse primer 2 | TCCATGCCCTGTGCAGTCTGTCGTG [SEQ ID NO: 45] |

TABLE 8-continued

V600D Reaction

| Oligonucleotide | Sequence and label (5'→3' for DNA and N→C for PNA) |
|---|---|
| Internal Control detectable oligonucleotide | Quasar-GFAFGAFAGAFLGFAFAGG-BHQ2-dT* [SEQ ID NO: 16] |

Example 5

The sequences used in this experiment are given above and in FIG. 1. FIG. 8 shows data from experiments wherein primers (the primers of FIG. 1) were made to distinguish between wild-type BRAF, BRAF with the V600E mutation and BRAF with the V600K mutation. In the first row (rows run from left to right; columns run from top to bottom) the wild-type or mutant designation is given for the target sequence. Below the target sequence designation is the nucleotide sequence for the 3' end of the target sequence. The sequence is underlined and the mutant nucleotides are in red. Below the sequence is the amino acid encoded by the given sequence.

For example, in the first block on the first row, the target sequence is named "WT1799a," the nucleotide sequence is "GTG" and the sequence encodes valine "Val(V)."

The first column of the Figure gives the 1) name of the primer and the sequence encoded by the 3' end of the primer, 2) the number of mismatches as compared to the target sequence, 3) the position of the mismatches from the 3' end of the subject sequence and, 4) the PCR result given in dCt (delta Concentration of target).

Thus, the box located at column 2, row 2 can be interpreted as indicating that the primer (MUf1b) for BRAF-T1799a, has two mismatches, the mismatches are located on the second and forth nucleotide and the dCt result was 9.35 when compared to the result for using the same primer for its intended target, T1799a. The dCt value for using a primer for its intended target is arbitrarily set to zero thus all results are relative to this value.

When the boxes at row 2, columns 2 and 3 are compared, it be seen that when a second mismatch is incorporated into the primer, the primer does not detect the wild-type target as efficiently as it does the intended target, the mutant BRAF, wherein there is only one mismatched nucleotide.

The genetic code is redundant allowing one amino acid to be encoded by more than one nucleotide trimer. In this regard, changes in a specific amino acid may be encoded by two or more different nucleotide mutations. FIG. 6 shows that primers designed to detect nucleotide mutations that result in the same amino acid change (e.g., V600E) do not detect these mutations as efficiently if the primers have more than one mutation relative to the specific target sequence as compared to primers that have a single nucleotide mismatch. Therefore, this data shows that the inventive concept described in the specification with regard to improved detection of SNPs is not limited to any particular sequence or intended target but, rather, is a concept that is broadly applicable to the improved detection of SNPs.

What is claimed is:

1. A composition comprising: a group of primers for amplification of a mutation (X) of the codon encoding valine at amino acid position 600 (V600X) in exon 15 of the BRAF (B-Raf proto-oncogene, serine/threonine kinase) gene in a sample of nucleic acid from a human,
wherein each primer is labeled and
wherein the group of primers is selected from groups 1-7 wherein:
(i) Group 1 consists of an oligonucleotide consisting of the nucleotide sequence GGTCTAGCTACNGAA [SEQ ID NO: 59] and an oligonucleotide consisting of the nucleotide sequence GGTCTAGCTACNGAG [SEQ ID NO: 60];
(ii) Group 2 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNAAA [SEQ ID NO: 46] at its 3' terminus and an oligonucleotide comprising the nucleotide sequence GGTCTAGC-TACNAAG [SEQ ID NO: 47] at its 3' terminus;
(iii) Group 3 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNGAT [SEQ ID NO: 48] at its 3' terminus and an oligonucleotide comprising the nucleotide sequence GGTCTAGC-TACNGAC [SEQ ID NO: 49] at its 3' terminus;
(iv) Group 4 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60]; an oligonucleotide comprising the nucleotide sequence GGTCTAGCTACNAAA [SEQ ID NO: 46] at its 3' terminus and an oligonucleotide comprising the nucleotide sequence GGTCTAGC-TACNAAG [SEQ ID NO: 47] at its 3' terminus, an oligonucleotide comprising the nucleotide sequence GGTCTAGCTACNGAT [SEQ ID NO: 48] at its 3' terminus and an oligonucleotide comprising the nucleotide sequence GGTCTAGCTACNGAC [SEQ ID NO: 49] at its 3' terminus;
(v) Group 5 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNAAT [SEQ ID NO: 50] at its 3' terminus and an oligonucleotide comprising the nucleotide sequence GGTCTAGC-TACNAAC [SEQ ID NO: 51] at its 3' terminus;
(vi) Group 6 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNCGT [SEQ ID NO: 52] at its 3' terminus, an oligonucleotide comprising the nucleotide sequence GGTCTAGC-TACNCGC [SEQ ID NO: 53] at its 3' terminus, an oligonucleotide comprising the nucleotide sequence GGTCTAGCTACNCGA [SEQ ID NO: 54] at its 3' terminus, an oligonucleotide comprising the nucleotide sequence GGTCTAGCTACNCGG [SEQ ID NO: 55] at its 3' terminus, an oligonucleotide comprising the nucleotide sequence GGTCTAGCTACN AGA [SEQ ID NO: 56] at its 3' terminus, and an oligonucleotide comprising the nucleotide sequence GGTCTAGCTACNAGG [SEQ ID NO: 57] at its 3' terminus; and
(vii) Group 7 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNAAT [SEQ ID NO: 50] at its 3' terminus, an oligonucleotide comprising the nucleotide sequence GGTCTAGC-TACNAAC [SEQ ID NO: 51] at its 3' terminus, an oligonucleotide comprising the nucleotide sequence GGTCTAGCTACNCGT [SEQ ID NO: 52] at its 3' terminus, an oligonucleotide comprising the nucleotide sequence GGTCTAGCTACNCGC [SEQ ID NO: 53] at its 3' terminus, an oligonucleotide comprising the nucleotide sequence GGTCTAGC-TACNCGA [SEQ ID NO: 54] at its 3' terminus, an oligonucleotide comprising the nucleotide sequence GGTCTAGCTACNCGG [SEQ ID NO: 55] at its 3' terminus, an oligonucleotide comprising the nucleotide sequence GGTCTAGCTACN AGA [SEQ ID NO: 56] at its 3' terminus, and an oligonucleotide comprising the nucleotide sequence GGTCTAGC-TACNAGG [SEQ ID NO: 57] at its 3' terminus;
wherein N is a nucleotide containing a base other than adenine (A),
wherein the primers of SEQ ID 46-57 comprise a length of from about 15 nucleotides to about 35 nucleotides;
and
wherein said label is selected from the group consisting of dyes, radioactive labels, electron-dense reagents, enzymes, haptens and proteins.

2. A kit comprising:
a group of primers for amplification of a mutation (X) of the codon encoding valine at amino acid position 600 (V600X) in exon 15 of the BRAF (B-Raf proto-oncogene, serine/threonine kinase) gene in a sample of nucleic acid from a human,
wherein each primer is labeled and
wherein the group of primers is selected from groups 1-7 wherein:
(i) Group 1 consists of an oligonucleotide consisting of the nucleotide sequence GGTCTAGCTACNGAA [SEQ ID NO: 59] and an oligonucleotide consisting of the nucleotide sequence GGTCTAGCTACNGAG [SEQ ID NO: 60];
(ii) Group 2 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNAAA [SEQ ID NO: 46] at its 3' terminus and an oligonucleotide comprising the nucleotide sequence GGTCTAGC-TACNAAG [SEQ ID NO: 47] at its 3' terminus;
(iii) Group 3 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNGAT [SEQ ID NO: 48] at its 3' terminus and an oligonucleotide comprising the nucleotide sequence GGTCTAGC-TACNGAC [SEQ ID NO: 49] at its 3' terminus;
(iv) Group 4 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60]; an oligonucleotide comprising the nucleotide sequence GGTCTAGCTACNAAA [SEQ ID NO: 46] at its 3' terminus and an oligonucleotide comprising the nucleotide sequence GGTCTAGC-TACNAAG [SEQ ID NO: 47] at its 3' terminus, an oligonucleotide comprising the nucleotide sequence GGTCTAGCTACNGAT [SEQ ID NO: 48] at its 3' terminus and an oligonucleotide comprising the nucleotide sequence GGTCTAGCTACNGAC [SEQ ID NO: 49] at its 3' terminus;
(v) Group 5 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNAAT [SEQ ID NO: 50] at its 3' terminus and an oligonucleotide comprising the nucleotide sequence GGTCTAGC-TACNAAC [SEQ ID NO: 51] at its 3' terminus;

(vi) Group 6 consists of an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNCGT [SEQ ID NO: 52] at its 3' terminus, an oligonucleotide comprising the nucleotide sequence GGTCTAGC-TACNCGC [SEQ ID NO: 53] at its 3' terminus, an oligonucleotide comprising the nucleotide sequence GGTCTAGCTACNCGA [SEQ ID NO: 54] at its 3' terminus, an oligonucleotide comprising the nucleotide sequence GGTCTAGCTACNCGG [SEQ ID NO: 55] at its 3' terminus, an oligonucleotide comprising the nucleotide sequence GGTCTAGCTACN AGA [SEQ ID NO: 56] at its 3' terminus, and an oligonucleotide comprising the nucleotide sequence GGTCTAGCTACNAGG [SEQ ID NO: 57] at its 3' terminus; and (vii) Group 7 consists of (an oligonucleotide consisting of the nucleotide sequence GGTCTAGCTACNGAA [SEQ ID NO: 59], an oligonucleotide consisting of the nucleotide sequence GGTCTAGCTACNGAG [SEQ ID NO: 60], an oligonucleotide comprising the nucleotide sequence GGTCTAGCTACNAAT [SEQ ID NO: 50] at its 3' terminus, an oligonucleotide comprising the nucleotide sequence GGTCTAGC-TACNAAC [SEQ ID NO: 51] at its 3' terminus, an oligonucleotide comprising the nucleotide sequence GGTCTAGCTACNCGT [SEQ ID NO: 52] at its 3' terminus, an oligonucleotide comprising the nucleotide sequence GGTCTAGCTACNCGC [SEQ ID NO: 53] at its 3' terminus, an oligonucleotide comprising the nucleotide sequence GGTCTAGC-TACNCGA [SEQ ID NO: 54] at its 3' terminus, an oligonucleotide comprising the nucleotide sequence GGTCTAGCTACNCGG [SEQ ID NO: 55] at its 3' terminus, an oligonucleotide comprising the nucleotide sequence GGTCTAGCTACN AGA [SEQ ID NO: 56] at its 3' terminus, and an oligonucleotide comprising the nucleotide sequence GGTCTAGC-TACNAGG [SEQ ID NO: 57] at its 3' terminus;

wherein N is a nucleotide containing a base other than adenine (A), wherein the primers of SEQ ID 46-57 comprise a length of from about 15 nucleotides to about 35 nucleotides; and wherein said label is selected from the group consisting of dyes, radioactive labels, electron-dense reagents, enzymes, haptens and proteins, and instructions for a method of detecting at least one mutation (X) of the codon encoding valine at amino acid position 600 (V600X) in exon 15 of the BRAF gene in a sample of nucleic acid from a human.

3. The kit of claim 2, wherein X is at least one amino acid selected from the group consisting of E (glutamic acid), K (lysine), D (aspartic acid), R (arginine), and N (asparagine).

4. The kit of claim 2, wherein X is at least one amino acid selected from the group consisting of E, K, and D.

5. The kit of claim 2, wherein X is E.

6. The kit of claim 2, wherein X is E and K, E and D, or K and D.

7. The kit of claim 2, wherein X is E, K, and D.

8. The Composition of claim 1, further comprising at least one PNA clamp.

9. The kit of claim 2, further comprising at least one PNA clamp.

10. The kit of claim 2, further comprising an internal control primer.

* * * * *

SEQUENCE LISTING

<160> NUMBER OF SEQ ID NOS: 61

<210> SEQ ID NO 1
<211> LENGTH: 41
<212> TYPE: DNA
<213> ORGANISM: Homo sapiens

<400> SEQUENCE: 1
aaataggtga ttttggtcta gctacagtga aatctcgatg g         41

<210> SEQ ID NO 2
<211> LENGTH: 41
<212> TYPE: DNA
<213> ORGANISM: Homo sapiens

<400> SEQUENCE: 2
aaataggtga ttttggtcta gctacagaga aatctcgatg g         41

<210> SEQ ID NO 3
<211> LENGTH: 41
<212> TYPE: DNA
<213> ORGANISM: Homo sapiens

<400> SEQUENCE: 3
aaataggtga ttttggtcta gctacagaaa aatctcgatg g         41

<210> SEQ ID NO 4
<211> LENGTH: 41

<212> TYPE: DNA
<213> ORGANISM: Homo sapiens

<400> SEQUENCE: 4
aaataggtga ttttggtcta gctacaaaga aatctcgatg g            41

<210> SEQ ID NO 5
<211> LENGTH: 41
<212> TYPE: DNA
<213> ORGANISM: Homo sapiens

<400> SEQUENCE: 5
aaataggtga ttttggtcta gctacaaaaa aatctcgatg g            41

<210> SEQ ID NO 6
<211> LENGTH: 41
<212> TYPE: DNA
<213> ORGANISM: Homo sapiens

<400> SEQUENCE: 6
aaataggtga ttttggtcta gctacagata aatctcgatg g            41

<210> SEQ ID NO 7
<211> LENGTH: 41
<212> TYPE: DNA
<213> ORGANISM: Homo sapiens

<400> SEQUENCE: 7
aaataggtga ttttggtcta gctacagaca aatctcgatg g            41

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aataggtgat tttggtctag ctaccgag                           28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aataggtgat tttggtctag ctaccgaa                           28

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taatcagtgg aaaaatagcc tcaattc                            27

<210> SEQ ID NO 11
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-FAM
<220> FEATURE:
<221> NAME/KEY: modified_base
<222> LOCATION: (1)..(1)
<223> OTHER INFORMATION: 5-Propynyl dU
<220> FEATURE:
<221> NAME/KEY: modified_base
<222> LOCATION: (6)..(6)
<223> OTHER INFORMATION: 5-Propynyl dU
<220> FEATURE:
<221> NAME/KEY: modified_base
<222> LOCATION: (10)..(10)
<223> OTHER INFORMATION: 5-Propynyl dU
<220> FEATURE:
<221> NAME/KEY: modified_base
<222> LOCATION: (11)..(13)
<223> OTHER INFORMATION: 5-Propynyl dC
<220> FEATURE:
<221> NAME/KEY: modified_base
<222> LOCATION: (15)..(15)
<223> OTHER INFORMATION: 5-Propynyl dU
<220> FEATURE:
<221> NAME/KEY: modified_base
<222> LOCATION: (16)..(16)
<223> OTHER INFORMATION: 5-Propynyl dC
<220> FEATURE:
<221> NAME/KEY: modified_base
<222> LOCATION: (19)..(20)
<223> OTHER INFORMATION: 5-Propynyl dU
<220> FEATURE:
<221> NAME/KEY: modified_base
<222> LOCATION: (21)..(21)
<223> OTHER INFORMATION: BHQ1-dT

<400> SEQUENCE: 11
uggagugggu cccaucaguu t                                            21

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gctacagtga aatctcg                                                 17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gctacaaaga aatctcg                                                 17

<210> SEQ ID NO 14
<211> LENGTH: 28
<212> TYPE: DNA
<213> ORGANISM: Artificial Sequence
<220> FEATURE:
```

<223> OTHER INFORMATION: Description of Artificial Sequence: Synthetic
    primer

<400> SEQUENCE: 14
gtatcaccat ctccatatca ttgagacc                                      28

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 15
acaagacatt taacgaatgg aacttactc                                     29

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<223> OTHER INFORMATION: 5'-Quasar
<220> FEATURE:
<221> NAME/KEY: modified_base
<222> LOCATION: (2)..(2)
<223> OTHER INFORMATION: 5-Propynyl dC
<220> FEATURE:
<221> NAME/KEY: modified_base
<222> LOCATION: (4)..(4)
<223> OTHER INFORMATION: 5-Propynyl dC
<220> FEATURE:
<221> NAME/KEY: modified_base
<222> LOCATION: (7)..(7)
<223> OTHER INFORMATION: 5-Propynyl dC
<220> FEATURE:
<221> NAME/KEY: modified_base
<222> LOCATION: (11)..(11)
<223> OTHER INFORMATION: 5-Propynyl dC
<220> FEATURE:
<221> NAME/KEY: modified_base
<222> LOCATION: (12)..(12)
<223> OTHER INFORMATION: 5-Propynyl dU
<220> FEATURE:
<221> NAME/KEY: modified_base
<222> LOCATION: (14)..(14)
<223> OTHER INFORMATION: 5-Propynyl dC
<220> FEATURE:
<221> NAME/KEY: modified_base
<222> LOCATION: (16)..(16)
<223> OTHER INFORMATION: 5-Propynyl dC
<220> FEATURE:
<221> NAME/KEY: modified_base
<222> LOCATION: (20)..(20)
<223> OTHER INFORMATION: BHQ2-dT

<400> SEQUENCE: 16
gcacgacaga cugcacaggt                                               20

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
    primer

```
<400> SEQUENCE: 17
aataggtgat tttggtctag ctactaag                                      28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aataggtgat tttggtctag ctactaaa                                      28

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gctacagaga aatctcg                                                  17

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aataggtgat tttggtctag ctactgat                                      28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aataggtgat tttggtctag ctactgac                                      28

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aataggtgat tttggtctag ctacaaa                                       27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
```
aataggtgat tttggtctag ctaccga                                27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aataggtgat tttggtctag ctacgga                                27

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aataggtgat tttggtctag ctactgag                               28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aataggtgat tttggtctag ctacggag                               28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aataggtgat tttggtctag ctactgaa                               28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aataggtgat tttggtctag ctacggaa                               28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
aataggtgat tttggtctag ctaccaag                                              28
```

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
aataggtgat tttggtctag ctacgaag                                              28
```

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
aataggtgat tttggtctag ctaccaaa                                              28
```

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
aataggtgat tttggtctag ctacgaaa                                              28
```

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
aataggtgat tttggtctag ctacaaac                                              28
```

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
aataggtgat tttggtctag ctacaaat                                              28
```

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
aataggtgat tttggtctag ctacaac                                               27
```

```
<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aataggtgat tttggtctag ctacgaa                                        27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aataggtgat tttggtctag ctaccaa                                        27

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gatctcagta aggtacggag taactgtc                                       28

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tagtctgttc ttttggatag catgaagct                                      29

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Quasar
<220> FEATURE:
<221> NAME/KEY: modified_base
<222> LOCATION: (3)..(3)
<223> OTHER INFORMATION: 5-Propynyl dU
<220> FEATURE:
<221> NAME/KEY: modified_base
<222> LOCATION: (10)..(11)
<223> OTHER INFORMATION: 5-Propynyl dC
<220> FEATURE:
<221> NAME/KEY: modified_base
<222> LOCATION: (13)..(13)
<223> OTHER INFORMATION: 5-Propynyl dC
<220> FEATURE:
```

```
<221> NAME/KEY: modified_base
<222> LOCATION: (14)..(14)
<223> OTHER INFORMATION: 5-Propynyl dU
<220> FEATURE:
<221> NAME/KEY: modified_base
<222> LOCATION: (15)..(15)
<223> OTHER INFORMATION: 5-Propynyl dC
<220> FEATURE:
<221> NAME/KEY: modified_base
<222> LOCATION: (16)..(18)
<223> OTHER INFORMATION: 5-Propynyl dU
<220> FEATURE:
<221> NAME/KEY: modified_base
<222> LOCATION: (19)..(20)
<223> OTHER INFORMATION: 5-Propynyl dC
<220> FEATURE:
<221> NAME/KEY: modified_base
<222> LOCATION: (21)..(21)
<223> OTHER INFORMATION: BHQ2-dT

<400> SEQUENCE: 40
gaugagagac cacucuuucc t                                              21

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctaaataagt ctttacaccc ccaagtatgt tc                                  32

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctgtggatga ttgacttggc gtgtaag                                        27

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-Quasar
<220> FEATURE:
<221> NAME/KEY: modified_base
<222> LOCATION: (4)..(6)
<223> OTHER INFORMATION: 5-Propynyl dU
<220> FEATURE:
<221> NAME/KEY: modified_base
<222> LOCATION: (7)..(7)
<223> OTHER INFORMATION: 5-Propynyl dC
<220> FEATURE:
<221> NAME/KEY: modified_base
<222> LOCATION: (12)..(13)
<223> OTHER INFORMATION: 5-Propynyl dC
<220> FEATURE:
<221> NAME/KEY: modified_base
<222> LOCATION: (18)..(18)
<223> OTHER INFORMATION: 5-Propynyl dU
```

```
<220> FEATURE:
<221> NAME/KEY: modified_base
<222> LOCATION: (19)..(20)
<223> OTHER INFORMATION: 5-Propynyl dC
<220> FEATURE:
<221> NAME/KEY: modified_base
<222> LOCATION: (21)..(21)
<223> OTHER INFORMATION: BHQ2-dT

<400> SEQUENCE: 43
agauuucgag gccagagucc t                                              21

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cacaaaatgg atccagacaa ctgttc                                         26

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tccatgccct gtgcagtctg tcgtg                                          25

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 46
ggtctagcta cnaaa                                                     15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 47
ggtctagcta cnaag                                                     15

<210> SEQ ID NO 48
<211> LENGTH: 15
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 48
ggtctagcta cngat                                                  15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 49
ggtctagcta cngac                                                  15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 50
ggtctagcta cnaat                                                  15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 51
ggtctagcta cnaac                                                  15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 52
ggtctagcta cncgt                                                  15

```
<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 53
ggtctagcta cncgc                                                    15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 54
ggtctagcta cncga                                                    15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 55
ggtctagcta cncgg                                                    15

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 56
ggtctagcta cnaga                                                    15

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
```

```
<223> OTHER INFORMATION: a, c, t, g, unknown or other

<400> SEQUENCE: 57
ggtctagcta cnagg                                                  15

<210> SEQ ID NO 58
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aataggtgat ttt                                                    13

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 59
ggtctagcta cngaa                                                  15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 60
ggtctagcta cngag                                                  15

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aataggtgat tttggtctag ctacaga                                     27
```